(12) United States Patent
Schnatterer et al.

(10) Patent No.: US 7,834,003 B2
(45) Date of Patent: Nov. 16, 2010

(54) 5-AMINOPYRAZOLE DERIVATIVES AS PESTICIDAL COMPOUNDS

(75) Inventors: Stefan Schnatterer, Hattersheim (DE); Michael Maier, Frankfurt (DE); Friederike Petry, Lauterbach (DE); Werner Knauf, Bad Bergzabern (DE); Karl Seeger, Hofheim (DE)

(73) Assignee: Merial Limited, Duluth, GA (US)

( * ) Notice: Subject to any disclaimer, the term of this patent is extended or adjusted under 35 U.S.C. 154(b) by 453 days.

(21) Appl. No.: 11/759,386

(22) Filed: Jun. 7, 2007

(65) Prior Publication Data
US 2008/0132487 A1 Jun. 5, 2008

Related U.S. Application Data

(63) Continuation-in-part of application No. PCT/EP2005/012903, filed on Dec. 2, 2005.

(30) Foreign Application Priority Data
Dec. 7, 2004 (EP) .................................. 04028940

(51) Int. Cl.
*A61K 31/55* (2006.01)
*A61K 31/541* (2006.01)
*C07D 417/02* (2006.01)
*C07D 413/02* (2006.01)

(52) U.S. Cl. .............. 514/217.1; 514/227.5; 514/235.5; 514/326; 514/365; 514/407; 544/60; 544/140; 544/371; 546/210; 548/364.1; 548/367.4

(58) Field of Classification Search ....................... None
See application file for complete search history.

(56) References Cited

U.S. PATENT DOCUMENTS
5,556,873 A * 9/1996 Huang et al. ................ 514/407

FOREIGN PATENT DOCUMENTS
EP 0295117 A1 12/1988
WO WO03074492 A2 9/2003
WO WO 2004/050633 6/2004

* cited by examiner

*Primary Examiner*—Kamal A Saeed
(74) *Attorney, Agent, or Firm*—Judy Jarecki-Black; Merial Limited; John Ezcurra

(57) ABSTRACT

The invention relates to 5-Aminopyrazole derivatives of formula (I) or salts thereof, a process for their preparation, to compositions thereof and to their use for the control of pests, including arthropods and helminths.

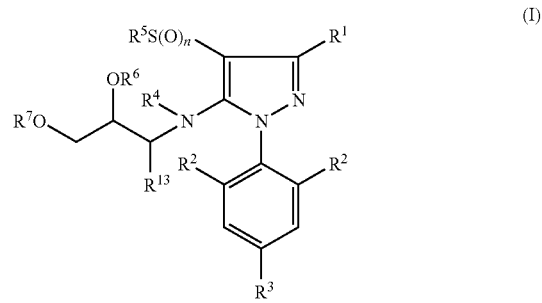

11 Claims, No Drawings

5-AMINOPYRAZOLE DERIVATIVES AS PESTICIDAL COMPOUNDS

This application is a continuation-in-part application of international patent application Serial No. PCT/EP2005/12903 filed Dec. 2, 2005, which published as PCT Publication No. WO 2006/061146 on Jun. 15, 2006, which claims benefit of European patent application Serial No. 04028940.7 filed Dec. 7, 2004.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any document in this application is not an admission that such document is available as prior art to the present invention. It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention. The embodiments of the present invention are disclosed herein or are obvious from and encompassed by, the detailed description. The detailed description, given by way of example, but not intended to limit the invention solely to the specific embodiments described, may best be understood in conjunction with the accompanying drawings.

The invention relates to 5-substituted N-phenylpyrazole derivatives, a process for their preparation and the use of the derivatives for the control of pests.

Several N-Phenylpyrazole compounds are already described as pesticides for the control of pests (e.g. in WO 87/03781, EP 02 95 117). However, modern pesticides must meet a wide range of demands, for example regarding level, duration and spectrum of action, use spectrum, toxicity, combination with other active substances, combination with formulation auxiliaries or synthesis. In particular the level of action and/or duration of action of these prior-art compounds is not entirely satisfactory in all fields of application, in particular against certain organisms or when low concentrations are applied.

To overcome some of the mentioned drawbacks novel 5-substituted-alkylaminopyrazole derivatives showing useful pesticidal properties are developed (WO 03/074492). But in consideration of the occurrence of resistances, the development of further substances can never be regarded as concluded, and there is constantly a high demand for novel alternative compounds which possess the advantages of the known compounds or even improved pesticidal properties, at least as far as some aspects are concerned.

The present invention provide 5-alkylaminopyrazole derivatives of formula (I):

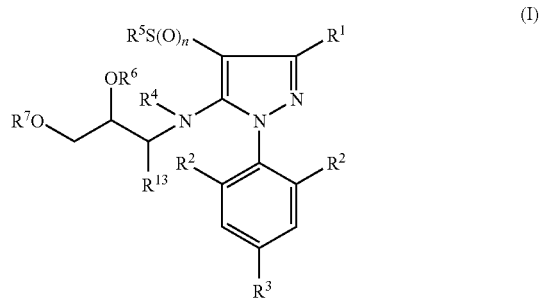

wherein
$R^1$ is CN, $CH_3$, $CF_3$, C(=N—Z)—$S(O)_p$—$(C_1$-$C_4)$-alkyl or $CSNH_2$;
wherein Z is H, $(C_1$-$C_6)$-alkyl, $(C_1$-$C_6)$-haloalkyl, $(C_3$-$C_6)$-alkenyl, $(C_3$-$C_6)$-alkynyl, —$(CH_2)_q R^8$, $COR^9$, $CO_2$—$(C_1$-$C_6)$-alkyl or $S(O)_p R^9$
$R^2$ for both residues independently from each other, is selected from the group consisting of halogen, $CH_3$ or $NR^{11}R^{12}$;
$R^3$ is $(C_1$-$C_3)$-haloalkyl, $(C_1$-$C_3)$-haloalkoxy or $SF_5$;
$R^4$ is hydrogen, $(C_2$-$C_6)$-alkenyl, $(C_2$-$C_6)$-haloalkenyl, $(C_2$-$C_6)$-alkynyl, $(C_2$-$C_6)$-haloalkynyl, $(C_3$-$C_7)$-cycloalkyl, $(C_3$-$C_7)$-cycloalkyl-$(C_1$-$C_6)$-alkyl, $CO_2$—$(C_1$-$C_6)$-alkyl, $CO_2$—$(C_3$-$C_6)$-alkenyl, $CO_2$—$(C_3$-$C_6)$-alkynyl, $CO_2$—$(CH_2)_q R^8$, $CO_2$—$(CH_2)_q R^{10}$ or $SO_2 R^9$; Formyl, CO—COO—$(C_1$-$C_6)$-alkyl or CO—$(C_1$-$C_6)$-alkyl unsubstituted or substituted by one or more radicals selected from the group consisting of halogen, $(C_1$-$C_6)$-alkoxy, $(C_1$-$C_6)$-haloalkoxy, $(C_3$-$C_6)$-alkenyloxy, $(C_3$-$C_6)$-haloalkenyloxy, $(C_3$-$C_6)$-alkynyloxy, $(C_3$-$C_6)$-haloalkynyloxy, $(C_3$-$C_7)$-cycloalkyl, $S(O)_p R^9$, CN, $NO_2$, OH, $R^8$, $R^{10}$, $COR^9$, $NR^{11}R^{12}$, $OR^9$ and $CO_2 R^9$; or CO—$(CH_2)_m R^8$; or CO—$(CH_2)_m R^{10}$; or $(C_1$-$C_6)$-alkyl unsubstituted or substituted by one or more radicals selected from the group consisting of halogen, $(C_1$-$C_6)$-alkoxy, $(C_1$-$C_6)$-haloalkoxy, $(C_3$-$C_6)$-alkenyloxy, $(C_3$-$C_6)$-haloalkenyloxy, $(C_3$-$C_6)$-alkynyloxy, $(C_3$-$C_6)$-haloalkynyloxy, $(C_3$-$C_7)$-cycloalkyl, $S(O)_p R^9$, CN, $NO_2$, OH, $R^8$, $R^{10}$, $COR^9$, $NR^{11}R^{12}$, $OR^9$ and $CO_2 R^9$;
$R^5$ is $(C_1$-$C_6)$-alkyl, $(C_1$-$C_6)$-haloalkyl, $(C_2$-$C_6)$-alkenyl, $(C_2$-$C_6)$-haloalkenyl, $(C_2$-$C_6)$-alkynyl or $(C_2$-$C_6)$-haloalkynyl;
$R^6$ and $R^7$ are each independently H; or $(C_1$-$C_6)$-alkyl, $(C_1$-$C_6)$-haloalkyl, $(C_2$-$C_6)$-alkenyl, $(C_2$-$C_6)$-alkynyl, all of them can be substituted by one or more $R^9$ or $OR^9$ radicals; or $R^8$, $R^{10}$; or are each independently Acyl groups of the type formyl, CO—$(C_1$-$C_6)$-alkyl, and CO—$(C_1$-$C_6)$-alkyl substituted by one or more $R^9$ radicals; or of the type COO—$(C_1$-$C_6)$-alkyl and COO—$(C_1$-$C_6)$-alkyl substituted by one or more $R^9$ radicals; or of the type $SO_2$—$(C_1$-$C_6)$-alkyl, and $SO_2$—$(C_1$-$C_6)$-alkyl unsubstituted or substituted by one or more $R^9$ radicals,
$R^6$ and $R^7$ may form together with the $C_2$-unit they are attached to a five to seven membered ring. In this case $R^6$ and $R^7$ together form divalent groups like CO, CS, CO—CO, $CH_2 CO$, $CHR^9 CO$, $CR^9 R^9 CO$, SO, $SO_2$, PO(OH), PO($OR^9$), PO($R^9$), PO($OR^{10}$), PO($R^{10}$), PO($OR^8$), PO($R^8$);
or like $(C_1$-$C_3)$-alkylene, $(C_3$-$C_7)$-cycloalkylene, $(C_3$-$C_7)$-cycloalkyl-$(C_1$-$C_6)$-alkylene, 1,2-phenylene, all of them unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$-haloalkynyloxy, $(C_3-C_7)$-cycloalkyl, $S(O)_pR^9$, CN, $NO_2$, OH, $R^8$, $R^{10}$, $COR^9$, $NR^{11}R^{12}$, $OR^9$ and $CO_2R^9$ $R^8$ is phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^9$ and $NR^{11}R^{12}$;

$R^9$ is $(C_1-C_6)$-alkyl, $(C_1-C_6)$-haloalkyl, $(C_3-C_7)$-cycloalkyl, $-(C_1-C_4)$-alkyl-$(C_3-C_7)$-cycloalkyl, $-(CH_2)_qR^8$ or $-(CH_2)_qR^{10}$ $R^{10}$ is heterocyclyl unsubstituted or substituted by one or more radicals selected from the group consisting of halogen, $(C_1-C_4)$-alkyl, $(C_1-C_4)$-haloalkyl, $(C_1-C_4)$-alkoxy, $S(O)_pR^{13}$, OH and oxo;

$R^{11}$ and $R^{12}$ are each independently H; or $(C_1-C_6)$-alkyl, $(C_1-C_6)$-haloalkyl, $(C_2-C_6)$-alkenyl, $(C_2-C_6)$-alkynyl, all of them can be substituted by one or more $R^9$ or $OR^9$ radicals;

$R^{13}$ is hydrogen, $(C_1-C_6)$-alkyl or phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^9$ and $NR^{11}R^{12}$;

n and p and q are each independently zero, one or two;

m is zero, one, two or three; and each heterocyclyl in the above-mentioned radicals is independently a heterocyclic radical having 3 to 7 ring atoms and 1, 2 or 3 hetero atoms in the ring selected from the group consisting of N, O and S;

or a pesticidally acceptable salt thereof.

The invention also encompasses any stereoisomer, enantiomer or geometric isomer, and mixtures of the compounds of formula (I).

By the term "pesticidally acceptable salts" are meant salts, the anions or cations of which are known and accepted in the art for the formation of salts for pesticidal use. Suitable salts with bases, e.g. formed by compounds of formula (I) containing a carboxylic acid group, include alkali metal (e.g. sodium and potassium), alkaline earth metal (e.g. calcium and magnesium), ammonium and amine (e.g. diethanolamine, triethanolamine, octylamine, morpholine and dioctylmethylamine) salts. Suitable acid addition salts, e.g. formed by compounds of formula (I) containing an amino group, including salts with inorganic acids, for example hydrochlorides, sulphates, phosphates and nitrates and salts with organic acids for example acetic acid.

In a further aspect of the invention there is provided the use of compounds of formula (I) or a pesticidally acceptable salt thereof for the control of parasites in and on animals.

A further aspect of the present invention there is provide the use of the compounds of formula (I) or a pesticidally acceptable salt thereof for preparing a veterinary medicament, preferably for the treatment of parasites, specifically ecto and endo parasites, in and on animals.

In the present patent specification, including the accompanying claims, the aforementioned substituents have the following meanings:

Halogen atom means fluorine, chlorine, bromine or iodine.

The term "halo" before the name of a radical means that this radical is partially or completely halogenated, that is to say, substituted by F, Cl, Br, or I, in any combination, preferably by F or Cl.

Alkyl groups and portions thereof (unless otherwise defined) may be straight- or branched-chain. The expression "$(C_1-C_6)$-alkyl" is to be understood as meaning an unbranched or branched hydrocarbon radical having 1, 2, 3, 4, 5 or 6 carbon atoms, such as, for example a methyl, ethyl, propyl, isopropyl, 1-butyl, 2-butyl, 2-methylpropyl or tert.-butyl radical.

Alkyl radicals and also in composite groups, unless otherwise defined, preferably have 1 to 4 carbon atoms.

"$(C_1-C_6)$-haloalkyl" means an alkyl group mentioned under the expression "$(C_1-C_6)$-alkyl" in which one or more hydrogen atoms are replaced by the same number of identical or different halogen atoms, such as monohaloalkyl, perhaloalkyl, $CF_3$, $CHF_2$, $CH_2F$, $CHFCH_3$, $CF_3CH_2$, $CF_3CF_2$, $CHF_2CF_2$, $CH_2FCHCl$, $CH_2Cl$, $CCl_3$, $CHCl_2$ or $CH_2CH_2Cl$.

"$(C_1-C_6)$-alkoxy" means an alkoxy group whose carbon chain has the meaning given under the expression "$(C_1-C_6)$-alkyl". "Haloalkoxy" is, for example, $OCF_3$, $OCHF_2$, $OCH_2F$, $CF_3CF_2O$, $OCH_2CF_3$ or $OCH_2CH_2Cl$.

"$(C_2-C_6)$-alkylene" is to be understood as meaning an unbranched or branched chain alkanediyl group having 1 to 6 carbon atoms, e.g. $-CH_2-$, $-CH_2-CH_2-$, $-CH_2-CH_2-CH_2-$ or $-CH_2-CH(CH_3)-$. The expression "$(C_1-C_6)$-haloalkene" means an $(C_1-C_6)$-alkylene group, in which one or more hydrogen atoms are replaced by the same number of identical or different halogen atoms.

"$(C_2-C_6)$-alkenyl" means an unbranched or branched non-cyclic carbon chain having a number of carbon atoms which corresponds to this stated range and which contains at least one double bond which can be located in any position of the respective unsaturated radical. "$(C_2-C_6)$-alkenyl" accordingly denotes, for example, the vinyl, allyl, 2-methyl-2-propenyl, 2-butenyl, pentenyl, 2-methylpentenyl or the hexenyl group.

"$(C_2-C_6)$-alkynyl" means an unbranched or branched non-cyclic carbon chain having a number of carbon atoms which corresponds to this stated range and which contains one triple bond which can be located in any position of the respective unsaturated radical. "$(C_2-C_6)$-alkynyl" accordingly denotes, for example, the propargyl, 1-methyl-2-propynyl, 2-butynyl or 3-butynyl group. Cycloalkyl groups preferably have from three to seven carbon atoms in the ring and are optionally substituted by halogen or alkyl.

In compounds of formula (I) the following examples of radicals are provided:

An example of alkyl substituted by cycloalkyl is cyclopropylmethyl;

an example of alkyl substituted by alkoxy is methoxymethyl ($CH_3OCH_2-$); and an example of alkyl substituted by alkylthio is methylthiomethyl ($CH_3SCH_2-$).

Aryl is a mono- or bicylic aromatic system, for example phenyl, naphthyl, tetrahydronaphthyl, indenyl, indanyl and the like, preferably phenyl.

A "heterocyclyl" group can be saturated, unsaturated or heteroaromatic; it preferably contains one or more, in particular 1, 2 or 3, hetero atoms in the heterocyclic ring, preferably selected from the group consisting of N, O and S; it is preferably an aliphatic heterocyclyl radical having 3 to 7 ring atoms or a heteroaromatic radical having 5 to 7 ring atoms. The heterocyclic radical can be, for example, a heteroaromatic radical or ring (heteroaryl) such as, for example, a mono-, bi- or polycyclic aromatic system in which at least 1 ring contains one or more hetero atoms, for example pyridyl, pyrimidinyl, pyridazinyl, pyrazinyl, triazinyl, thienyl, thiazolyl, thiadiazolyl, oxazolyl, isoxazolyl, furyl, pyrrolyl, pyrazolyl, imidazolyl and triazolyl, or it is a partially or fully hydrogenated radical such as oxiranyl, oxetanyl, oxolanyl (=tetrahydrofuryl), oxanyl, pyrrolidyl, piperidyl, piperazinyl, dioxolanyl, oxazolinyl, isoxazolinyl, oxazolidinyl, isoxazolidinyl and morpholinyl. The "heterocyclyl" group may be unsubstituted or substituted by one or radicals (preferably 1, 2 or 3 radicals) selected from the group consisting of halogen, alkoxy, haloalkoxy, alkylthio, hydroxyl, amino, nitro, carboxyl, cyano, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl, alkyl and haloalkyl, and additionally also oxo. The oxo group can also be present at those hetero ring atoms where various oxidation numbers are possible, for example in the case of N and S.

Preferred embodiments of the present invention encompass compounds of formula (I) in which preferably $R^1$ is CN, C(=N—Z)—S(O)$_p$—(C$_1$-C$_4$)-alkyl or CSNH$_2$; wherein Z is H, (C$_1$-C$_3$)-alkyl, —(CH$_2$)$_q$R$^8$, COR$^9$, CO$_2$—(C$_1$-C$_3$)-alkyl or S(O)$_p$R$^9$; and/or $R^2$ is halogen, in particular F or Cl
and/or $R^3$ is (C$_1$-C$_3$)-haloalkyl; in particular CF$_3$ or OCF$_3$ (more preferably CF$_3$) and/or $R^5$ is (C$_1$-C$_3$)-haloalkyl; in particular CF$_3$ or OCF$_3$ (more preferably CF$_3$) and/or $R^{13}$ is hydrogen, (C$_1$-C$_3$)-alkyl, unsubstituted or substituted by one or more halogen.

Preferably $R^4$ is hydrogen, (C$_2$-C$_4$)-alkenyl, (C$_2$-C$_4$)-haloalkenyl, (C$_2$-C$_4$)-alkynyl, (C$_2$-C$_4$)-haloalkynyl, (C$_3$-C$_7$)-cycloalkyl, (C$_3$-C$_7$)-cycloalkyl-(C$_1$-C$_4$)-alkyl, CO$_2$—(C$_1$-C$_4$)-alkyl, CO$_2$—(C$_3$-C$_4$)-alkenyl, CO$_2$—(C$_3$-C$_4$)-alkynyl, CO$_2$—(CH$_2$)$_q$R$^8$, CO$_2$—(CH$_2$)$_q$R$^{10}$ or SO$_2$R$^9$; Formyl, CO—COO—(C$_1$-C$_4$)-alkyl, CO—(C$_1$-C$_4$)-alkyl or (C$_1$-C$_4$)-alkyl, unsubstituted or substituted by one or more radicals selected from the group consisting of halogen, (C$_1$-C$_3$)-alkyl, (C$_1$-C$_3$)-haloalkyl, (C$_1$-C$_3$)-alkoxy, (C$_1$-C$_3$)-haloalkoxy, S(O)$_p$R$^9$, CN and NO$_2$. More preferably $R^4$ is hydrogen, CO$_2$—(C$_1$-C$_3$)-alkyl, SO$_2$R$^9$, (C$_1$-C$_3$)-alkyl, unsubstituted or substituted by one or more radicals selected from the group consisting of halogen, (C$_1$-C$_3$)-alkoxy, CO$_2$—(C$_1$-C$_3$)-alkyl, S(O)$_p$R$^9$, wherein each R$^9$ is selected from the group consisting of (C$_1$-C$_3$)-alkyl or (C$_1$-C$_3$)-haloalkyl. Most preferably $R^4$ is (C$_1$-C$_3$)-alkyl.

Preferred embodiments of the present invention encompass further compounds of formula (I) in which independently from one another $R^6$ and $R^7$ is hydrogen, (C$_1$-C$_6$)-alkyl, (C$_1$-C$_6$)-haloalkyl, (C$_2$-C$_6$)-alkenyl, or (C$_2$-C$_6$)-alkynyl, in all of them one or more hydrogen can be substituted by one or more radicals R$^9$ or OR$^9$; or R$^8$, R$^{10}$; or are each independently Acyl groups of the type formyl, CO—(C$_1$-C$_6$)-alkyl, and CO—(C$_1$-C$_6$)-alkyl substituted by one or more radicals R$^9$; or of the type COO—(C$_1$-C$_6$)-alkyl and COO—(C$_1$-C$_6$)-alkyl substituted by one or more R$^9$ radicals; or of the type CO—COO—(C$_1$-C$_6$)-alkyl and CO—COO—(C$_1$-C$_6$)-alkyl substituted by one or more R$^9$ radicals; or of the type SO$_2$—(C$_1$-C$_6$)-alkyl, and SO$_2$—(C$_1$-C$_6$)-alkyl unsubstituted or substituted by one or more R$^9$ radicals, wherein
$R^6$ and $R^7$ may form together with the C$_2$-unit they are attached to a five to seven membered ring. In this case $R^6$ and $R^7$ together form divalent groups like CO, CS, CO—CO, CH$_2$CO, SO, SO$_2$, PO(OH), PO(OR$^8$), PO(R$^8$), PO(OR$^9$), PO(R$^9$); or like (C$_1$-C$_3$)-alkylene, (C$_3$-C$_7$)-cycloalkylene, (C$_3$-C$_7$)-cycloalkyl-(C$_1$-C$_6$)-alkylene, 1,2-phenylene, all of them unsubstituted or substituted by one or more radicals selected from the group consisting of halogen, (C$_1$-C$_6$)-alkoxy, (C$_1$-C$_6$)-haloalkoxy, (C$_3$-C$_6$)-alkenyloxy, (C$_3$-C$_6$)-haloalkenyloxy, (C$_3$-C$_6$)-alkynyloxy, (C$_3$-C$_6$)-haloalkynyloxy, (C$_3$-C$_7$)-cycloalkyl, S(O)$_p$R$^9$, CN, NO$_2$, OH, R$^8$, R$^{10}$, COR$^9$, NR$^{11}$R$^{12}$, OR$^9$ and CO$_2$R$^9$.

Specifically compounds of formula (I) wherein at least one of the residues R$^6$ and R$^7$ is selected from the group consisting of formyl, CO—(C$_1$-C$_6$)-alkyl, CO—(C$_1$-C$_6$)-alkyl substituted by one or more radicals R$^9$; COO—(C$_1$-C$_6$)-alkyl, COO—(C$_1$-C$_6$)-alkyl substituted by one or more radicals R$^9$; CO—COO—(C$_1$-C$_6$)-alkyl, CO—COO—(C$_1$-C$_6$)-alkyl substituted by one or more radicals R$^9$; SO$_2$—(C$_1$-C$_6$)-alkyl, SO$_2$—(C$_1$-C$_6$)-alkyl substituted by one or more radicals R$^9$ or wherein R$^6$ and R$^7$ together form a divalent group selected from the group consisting of CO, CS, CO—CO, CH$_2$CO, SO, SO$_2$, PO(OH), PO(OR$^9$), PO(R$^9$), PO(OR$^8$), PO(R$^8$) are preferred.

In particular preferred embodiments of the present invention are compounds of formula (I) wherein
$R^1$ is CN;
$R^2$ is halogen;
$R^3$ is (C$_1$-C$_3$)-haloalkyl;
$R^4$ is hydrogen, (C$_2$-C$_6$)-alkenyl, (C$_2$-C$_6$)-haloalkenyl, (C$_2$-C$_6$)-alkynyl, (C$_2$-C$_6$)-haloalkynyl, (C$_3$-C$_7$)-cycloalkyl, (C$_3$-C$_7$)-cycloalkyl-(C$_1$-C$_6$)-alkyl, CO$_2$—(C$_1$-C$_6$)-alkyl, CO$_2$—(C$_3$-C$_6$)-alkenyl, CO$_2$—(C$_3$-C$_6$)-alkynyl, CO$_2$—(CH$_2$)$_q$R$^8$, CO$_2$—(CH$_2$)$_q$R$^{10}$ or SO$_2$R$^9$; Formyl, CO—COO—(C$_1$-C$_6$)-alkyl or CO—(C$_1$-C$_6$)-alkyl unsubstituted or substituted by one or more radicals selected from the group consisting of halogen, (C$_1$-C$_6$)-alkoxy, (C$_1$-C$_6$)-haloalkoxy, (C$_3$-C$_6$)-alkenyloxy, (C$_3$-C$_6$)-haloalkenyloxy, (C$_3$-C$_6$)-alkynyloxy, (C$_3$-C$_6$)-haloalkynyloxy, (C$_3$-C$_7$)-cycloalkyl, S(O)$_p$R$^9$, CN, NO$_2$, OH, R$^8$, R$^{10}$, COR$^9$, NR$^{11}$R$^{12}$, OR$^9$ and CO$_2$R$^9$; or CO—(CH$_2$)$_n$R$^8$; or CO—(CH$_2$)$_n$R$^{10}$; or $R^4$ is (C$_1$-C$_6$)-alkyl
unsubstituted or substituted by one or more radicals selected from the group consisting of halogen, (C$_1$-C$_6$)-alkoxy, (C$_1$-C$_6$)-haloalkoxy, (C$_3$-C$_6$)-alkenyloxy, (C$_3$-C$_6$)-haloalkenyloxy, (C$_3$-C$_6$)-alkynyloxy, (C$_3$-C$_6$)-haloalkynyloxy, (C$_3$-C$_7$)-cycloalkyl, S(O)$_p$R$^9$, CN, NO$_2$, OH, R$^8$, R$^{10}$, COR$^9$, NR$^{11}$R$^{12}$OR$^9$ and CO$_2$R$^9$;
$R^5$ is (C$_1$-C$_6$)-alkyl, (C$_1$-C$_6$)-haloalkyl;
$R^6$ and $R^7$ are each independently H; or (C$_1$-C$_6$)-alkyl, (C$_1$-C$_6$)-haloalkyl, (C$_2$-C$_6$)-alkenyl, (C$_2$-C$_6$)-alkynyl, all of them can be substituted by one or more R$^9$ or OR$^9$ radicals; or R$^8$, R$^{10}$; or are each independently Acyl groups of the type formyl, CO—(C$_1$-C$_6$)-alkyl, and CO—(C$_1$-C$_6$)-alkyl substituted by one or more R$^9$ radicals; or of the type COO—(C$_1$-C$_6$)-alkyl and COO—(C$_1$-C$_6$)-alkyl substituted by one or more R$^9$ radicals; or of the type CO—COO—(C$_1$-C$_6$)-alkyl and CO—COO—(C$_1$-C$_6$)-alkyl substituted by one or more R$^9$ radicals; or of the type SO$_2$—(C$_1$-C$_6$)-alkyl, and SO$_2$—(C$_1$-C$_6$)-alkyl substituted by one or more R$^9$ radicals, wherein $R^6$ and $R^7$ may form together with the C$_2$-unit they are attached to a five to seven membered ring. In this case R$^6$ and R$^7$ together form divalent groups like CO, CS, CO—CO, CH$_2$CO, SO, SO$_2$, PO(OH), PO(OR$^9$), PO(R$^9$) PO(OR$^8$), PO(R$^8$); or like (C$_1$-C$_3$)-alkylene, (C$_3$-C$_7$)-cycloalkylene, (C$_3$-C$_7$)-cycloalkyl-(C$_1$-C$_6$)-alkylene, 1,2-phenylene, all of them unsubstituted or substituted by one or more radicals selected from the group consisting of halogen, (C$_1$-C$_6$)-alkoxy, (C$_1$-C$_6$)-haloalkoxy, (C$_3$-C$_6$)-alkenyloxy, (C$_3$-C$_6$)-haloalkenyloxy, (C$_3$-C$_6$)-alkynyloxy, (C$_3$-C$_6$)-haloalkynyloxy, (C$_3$-C$_7$)-cycloalkyl, S(O)$_p$R$^9$, CN, NO$_2$, OH, R$^8$, R$^{10}$, COR$^9$, NR$^{11}$R$^{12}$OR$^9$ and CO$_2$R$^9$.
$R^8$ is phenyl unsubstituted or substituted by one or more radicals selected from the group consisting of halogen, (C$_1$-C$_6$)-alkyl, (C$_1$-C$_6$)-haloalkyl, (C$_1$-C$_6$)-alkoxy, (C$_1$-C$_6$)-haloalkoxy, CN, NO$_2$, S(O)$_p$R$^9$ and NR$^{11}$R$^{12}$;
$R^9$ is (C$_1$-C$_6$)-alkyl, (C$_1$-C$_6$)-haloalkyl, (C$_3$-C$_7$)-cycloalkyl, —(C$_1$-C$_4$)-alkyl-(C$_3$-C$_7$)-cycloalkyl, —(CH$_2$)$_q$R$^8$ or —(CH$_2$)$_q$R$^{10}$ $R^{10}$ is heterocyclyl unsubstituted or substituted by one or more radicals selected from the group consisting of halogen, $(C_1-C_4)$-alkyl, $(C_1-C_4)$-haloalkyl, $(C_1-C_4)$-alkoxy, $S(O)_pR^{13}$, OH and oxo;

$R^{11}$ and $R^{12}$ are each independently H; or $(C_1-C_6)$-alkyl, $(C_1-C_6)$-haloalkyl, $(C_2-C_6)$-alkenyl, $(C_2-C_6)$-alkynyl, all of them can be substituted by one or more $R^9$ or $OR^9$ radicals;

$R^{13}$ is hydrogen, $(C_1-C_6)$-alkyl or phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^9$ and $NR^{11}R^{12}$;

Most preferred compounds in accordance with the present invention are substances of formula (I) wherein $R^1$ is CN;
$R^2$ is Cl;
$R^3$ is $CF_3$;
$R^4$ is hydrogen; or $(C_1-C_6)$-alkyl unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$-haloalkynyloxy, $(C_3-C_7)$-cycloalkyl, $S(O)_pR^9$, CN, $NO_2$, OH, $R^8$, $R^{10}$, $COR^9$; $NR^{11}R^{12}$, $OR^9$ and $CO_2R^9$;
$R^5$ is $CF_3$;
$R^6$ and $R^7$ are each independently H; or $(C_1-C_6)$-alkyl, $(C_1-C_6)$-haloalkyl, $(C_2-C_6)$-alkenyl, $(C_2-C_6)$-alkynyl, all of them can be substituted by one or more $R^9$ or $OR^9$ radicals; or $R^8$, $R^{10}$; or are each independently Acyl groups of the type formyl, CO—$(C_1-C_6)$-alkyl, and CO—$(C_1-C_6)$-alkyl substituted by one or more $R^9$ radicals; or of the type COO—$(C_1-C_6)$-alkyl and COO—$(C_1-C_6)$-alkyl substituted by one or more $R^9$ radicals; or of the type CO—COO—$(C_1-C_6)$-alkyl and CO—COO—$(C_1-C_6)$-alkyl substituted by one or more $R^9$ radicals; or of the type $SO_2$—$(C_1-C_6)$-alkyl, and $SO_2$—$(C_1-C_6)$-alkyl substituted by one or more $R^9$ radicals wherein $R^6$ and $R^7$ may form together with the $C_2$-unit they are attached to a five to seven membered ring. In this case $R^6$ and $R^7$ together form divalent groups like CO, CS, CO—CO, $CH_2CO$, SO, $SO_2$, PO(OH), $PO(OR^9)$, $PO(R^9)$, $PO(OR^8)$, $PO(R^8)$; or like $(C_1-C_3)$-alkylene, $(C_3-C_7)$-cycloalkylene, $(C_3-C_7)$-cycloalkyl-$(C_1-C_6)$-alkylene, 1,2-phenylene, all of them unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$-haloalkynyloxy, $(C_3-C_7)$-cycloalkyl, $S(O)_pR^9$, CN, $NO_2$, OH, $R^8$, $R^{10}$, $COR^9$, $NR^{11}R^{12}$, $OR^9$ and $CO_2R^9$ $R^8$ is phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^9$ and $NR^{11}R^{12}$;

$R^9$ is $(C_1-C_6)$-alkyl, $(C_1-C_6)$-haloalkyl, $(C_3-C_7)$-cycloalkyl, —$(C_1-C_4)$-alkyl-$(C_3-C_7)$-cycloalkyl, —$(CH_2)_qR^8$ or —$(CH_2)_qR^{10}$ $R^{10}$ is heterocyclyl unsubstituted or substituted by one or more radicals selected from the group consisting of halogen, $(C_1-C_4)$-alkyl, $(C_1-C_4)$-haloalkyl, $(C_1-C_4)$-alkoxy, $S(O)_pR^{13}$, OH and oxo;

$R^{11}$ and $R^{12}$ are each independently H; or $(C_1-C_6)$-alkyl, $(C_1-C_6)$-haloalkyl, $(C_2-C_6)$-alkenyl, $(C_2-C_6)$-alkynyl, all of them can be substituted by one or more $R^9$ or $OR^9$ radicals;

$R^{13}$ is hydrogen, $(C_1-C_6)$-alkyl or phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^9$ and $NR^{11}R^{12}$.

A further preferred class of compounds of formula (I) are those wherein $R^1$ is CN;
$R^2$ is Cl;
$R^3$ and $R^5$ is $CF_3$;
$R^4$ and $R^{13}$ is independently from one another hydrogen or $CH_3$ $R^6$ and $R^7$ is independently from one another hydrogen, phenyl (Ph) or $(C_1-C_5)$-alkyl, in particular methyl (Me), ethyl (Et), n-propyl (nPr), iso-propyl (iPr), n-butyl (nBu), sec.-butyl (secBu), iso-butyl (iBu), tert.-butyl (tBu), n-pentyl ($nC_5H_{11}$), n-hexyl ($nC_6H_{13}$)

A further preferred class of compounds of formula (I) are those wherein $R^1$ is CN;
$R^2$ is Cl;
$R^3$ and $R^5$ is $CF_3$;
$R^4$ and $R^{13}$ is independently from one another hydrogen or $CH_3$ $R^6$ and $R^7$ is independently from one another a CO—$(C_1-C_4)$-alkyl, COO—$(C_1-C_4)$-alkyl or CO—COO—$(C_1-C_4)$-alkyl radical in particular selected from the group consisting of HCO, $CH_3CO$, $C_2H_5CO$, $n-C_3H_7CO$, iso-$C_3H_7CO$, $n-C_4H_9CO$, tert.-butyl-CO (tBuCO), iso-$C_4H_9CO$ (iBuCO), sec.-butyl-CO (secBuCO), Phenyl-CO (PhCO), $CH_3OCH_2CO$ ($MeOCH_2CO$), $CH_3OCO$ (MeOCO), $C_2H_5OCO$ (EtOCO), $n-C_3H_7OCO$ (nPrOCO), iso-$C_3H_7OCO$ (iPrOCO), $n-C_4H_9OCO$ (nBuOCO), iso-$C_4H_9OCO$ (iBuOCO), tert.-$C_4H_9OCO$ (tBuOCO), sec.-$C_4H_9OCO$ (secBuOCO), CO—COO—$CH_3$ (CO—COOMe), CO—COO—$C_2H_5$ (CO—COOEt), CO—COO-$n-C_3H_7$ (CO—COOnPr), CO—COO-iso-$C_3H_7$ (CO—COOiPr), CO—COO-n-$C_4H_9$ (CO—COOnBu), CO—COO-iso-$C_3H_7$ (CO—COOiBu), CO—COO-ter.-$C_4H_9$ (CO—COOtBu), CO—COO-sec.-$C_4H_9$ (CO—COOsecBu).

A further preferred class of compounds of formula (I) are those wherein $R^1$ is CN;
$R^2$ is Cl;
$R^3$ and $R^5$ is $CF_3$;
$R^4$ and $R^{13}$ is independently from one another hydrogen or $CH_3$ and wherein $R^6$ and $R^7$ form together with the $C_2$-unit they are attached to a five to seven membered ring. The divalent groups formed by $R^6$ and $R^7$ is in particular selected from the group consisting of $CH_2$, $C(CH_3)_2$ ($CMe_2$), $C_2H_4$, $C_3H_6$, Phenyl-CH(CHPh), 1,2-$C_6H_4$, cyclopentan-1,1-diyl and cyclohexan-1,1-diyl.

A further preferred class of compounds of formula (I) are those wherein $R^1$ is CN;
$R^2$ is Cl;
$R^3$ and $R^5$ is $CF_3$;
$R^4$ and $R^{13}$ is independently from one another hydrogen or $CH_3$ and wherein $R^6$ and $R^7$ form together with the $C_2$-unit they are attached to a five to seven membered ring. The divalent groups formed by $R^6$ and $R^7$ is in particular selected from the group consisting of CO, CS, CO—CO, $CH_2CO$, SO, $SO_2$, PO(OH), $PO(OR^9)$, $PO(R^9)$, $PO(OR^8)$ and $PO(R^8)$, wherein $R^9$ is most preferably a $(C_1-C_3)$-alkyl radical and $R^8$ is most preferably a phenyl radical.

General Processes for the Synthesis of Compounds of Formula (I)

The compounds of general formula (I) can be prepared by the application or adaptation of known methods (i.e. methods heretofore used or described in the chemical literature).

In the following description of processes when symbols appearing in formulae are not specifically defined, it is understood that they are "as defined above" in accordance with the first definition of each symbol in the specification.

According to a further feature of the invention compounds of formula (I) wherein $R^1$ is CN, $CH_3$ or $CF_3$, and $R^2$, $R^3$, $R^5$ and n are as defined above, may be prepared by the reaction of a compound of formula (II):

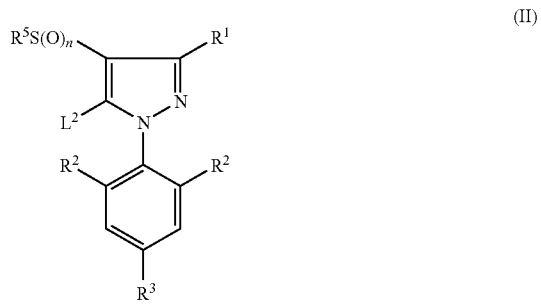

wherein $L^2$ is a leaving group generally halogen and preferably bromine, and the other values are as defined above, with a compound of formula (III):

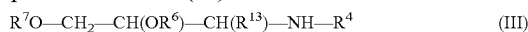

wherein $R^4$, $R^6$, $R^7$ and $R^{13}$ are as defined above.

The reaction is preferably performed in the presence of a base such as an alkali metal hydride such as sodium hydride, or an alkali metal carbonate such as potassium carbonate or sodium carbonate, or an organic base such as a tertiary amine, for example triethylamine or ethyldiisopropylamine, in a solvent such as tetrahydrofuran, dioxan or acetonitrile, at a temperature of from 20° C. to 150° C.

According to a further feature of the invention compounds of formula (I) wherein $R^1$ is CN, $CH_3$ or $CF_3$, and $R^2$, $R^3$, $R^4$, $R^5$, n and the other values are as defined above, may be prepared by the reaction of a compound of formula (IV):

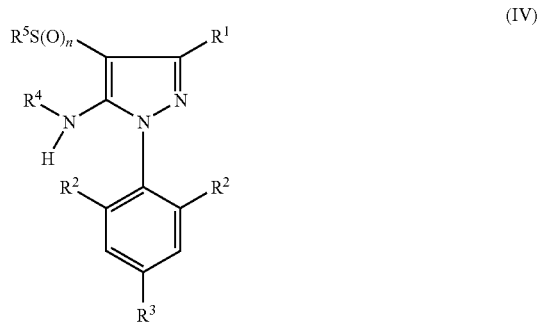

with an alkylating agent of formula (III):

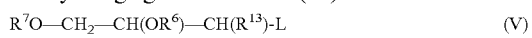

wherein $R^6$, $R^7$ and $R^{13}$ are as defined above, and L is a leaving group generally halogen and preferably chlorine, bromine or iodine, and a base.

The reaction is generally carried out using a solvent such as tetrahydrofuran, dioxan or acetonitrile, at a temperature of from 20° C. to 120° C.

The base is preferably an alkali metal hydride such as sodium hydride, or an alkali metal carbonate such as potassium carbonate or sodium carbonate, or an alkali metal phosphate such as potassium phosphate, or an organic base such as a tertiary amine, for example triethylamine or ethyldiisopropylamine. Alkali metal phosphates such as potassium phosphate are particularly preferred.

According to a further feature of the invention compounds of formula (I) wherein $R^1$ is CN, $CH_3$ or $CF_3$, and $R^2$, $R^3$, $R^4$, $R^5$, $R^{13}$ and n and the other values are as defined above, may be prepared by the reaction of a compound of formula (Ia), and wherein $R^6$, $R^7$ is H:

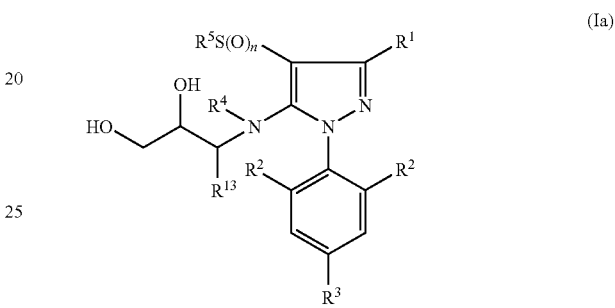

with an acylation agent selected from the group $R^{14}$—COCl or $R^{14}$—CO—O—CO—$R^{15}$ or an acid dichloride from the group phosgene, oxalylchloride, thionylchloride, phosphorusdichlorides and a base. Preferably $R^{14}$ and $R^{15}$ are independently H or $(C_1\text{-}C_6)$-alkyl, wherein the alkyl residue may be unsubstituted or substituted by one or more radicals $R^9$.

The reaction is generally carried out using a solvent such as tetrahydrofuran, dioxan or acetonitrile, at a temperature of from 20° C. to 120° C. The base is preferably an organic base such as a tertiary amine, for example triethylamine or ethyldiisopropylamine.

According to a further feature of the present invention compounds of formula (I) wherein $R^1$ is $CSNH_2$ and the other residues and values are as defined above may be prepared by reaction of the corresponding compound of formula (I) wherein $R^1$ is CN, with an alkali or alkaline earth metal hydrosulfide, such as lithium, potassium, calcium or preferably sodium hydrosulfide, in an inert solvent for example N,N-dimethylformamide, pyridin, dioxan, tetrahydrofuran, sulfolane, dimethyl sulfoxide, methanol or ethanol at a temperature from −35° C. to 50° C., preferably 0° C. to 30° C. Optionally the hydrosulfide may be generated in situ by treatment with $H_2S$ in presence of an organic base, such as metal alkoxide or trialkylamine or an inorganic base, such as sodium, potassium or ammonium carbonate. The use of a metal complexing agent, such as crown ether, can be benefit in accelerating the reaction. The reaction of hydrosulfide salt with the compound of formula (Ia), (II) or (IV) can also be conducted in a two-phase water/organic solvent system using a phase transfer catalyst such as a crown ether or a tetraalkylammonium salt such as tetra-n-butylammonium bromide or benzyltrimethylammonium chlorine. Organic solvents suitable for use in a two phase system with water include benzene, toluene, dichloromethane, 1-chlorobutane and methyl tertiary-butyl ether.

Alternatively compounds of formula (I) wherein $R^1$ is $CSNH_2$, may also be prepared from the corresponding compound of formula (I) wherein $R^1$ is CN, by treatment with the reagent $Ph_2PS_2$, as described in Tet. Lett., 24 (20), 2059 (1983).

According to a further feature of the invention compounds of formula (I) wherein $R^1$ is $CSNH_2$ and the other residues and values are as defined above, may be prepared by the reaction of the corresponding compound of formula (I) wherein $R^1$ is CN, with a bis(trialkylsilyl)sulfide, preferably bis(trimethylsilyl)sulfide, in the presence of a base generally an alkali metal alkoxide such as sodium methoxide, in a solvent such as N,N-dimethylformamide, at a temperature of from 0° C. to 60° C. The procedure is generally described by Lin, Ku and Shiao in Synthesis 1219 (1992).

According to a further feature of the invention compounds of formula (I) wherein $R^1$ is C(=N—H)—S—$(C_1-C_4)$-alkyl and the other residues and values are as defined above, may be prepared by the reaction of the corresponding compound of formula (I) wherein $R^1$ is $CSNH_2$ with an alkylating agent of formula (VI) or (VI):

$(C_1-C_4)$-alkyl-$L^3$ (VI)

$((C_1-C_4)\text{-alkyl})_3O^+BF_4^-$ (VII)

wherein $L^3$ is a leaving group, generally halogen and preferably chlorine, bromine or iodine. The reaction is generally performed in the presence of a base, for example an alkali metal hydride such as sodium hydride, or an alkali metal alkoxide such as potassium tert-butoxide, in an inert solvent such as tetrahydrofuran at a temperature from 0° C. to 60° C. Alternatively an alkali metal carbonate such as potassium carbonate, or an organic base such as a trialkylamine, for example triethylamine or N,N-diisopropylethylamine may be used, in an inert solvent such as acetone, at a temperature from 0° C. to the reflux temperature of the solvent. When a compound of formula (VII) such as trimethyloxonium tetrafluoroborate is used as the alkylating agent, the base is preferably an alkali metal bicarbonate such as sodium bicarbonate, the solvent is for example dichloromethane, and the temperature is from 0° C. to the reflux temperature of the solvent.

According to a further feature of the present invention compounds of formula (I) wherein $R^1$ is C(=N—Z)—S—$(C_1-C_4)$-alkyl, Z is as defined above with the exclusion of H, and the other values are as defined in formula (I), may be prepared by the alkylation, acylation or sulfonylation of the corresponding compound of formula (I) wherein Z is H, with a compound of formula (VIII):

Z-$L^4$ (VIII)

wherein Z is defined above with the exclusion of H and wherein $L^4$ is a leaving group. For alkylations, where Z is $(C_1-C_6)$-alkyl, $(C_1-C_6)$-haloalkyl, $(C_3-C_6)$-alkenyl, $(C_3-C_6)$-alkynyl or —$(CH_2)_qR^7$, $L^4$ is preferably halogen, alkylsulfonyloxy or arylsulfonyloxy (more preferably chlorine, bromine, iodine, methylsulfonyloxy or p-toluenesulfonyloxy). A base is optionally present in the reaction which is generally performed in an inert solvent such as tetrahydrofuran, dioxan, acetonitrile, toluene, diethyl ether, dichloromethane, dimethylsulfoxide or N,N-dimethylformamide, at a temperature of from −30° C. to 200° C., preferably at 20° C. to 100° C. The base is generally an alkali metal hydroxide such as potassium hydroxide, an alkali metal hydride such as sodium hydride, an alkali metal carbonate such as potassium carbonate or sodium carbonate, an alkali metal alkoxide such as sodium methoxide, an alkaline earth metal carbonate such as calcium carbonate, or an organic base such as a tertiary amine, for example triethylamine or ethyldiisopropylamine, or pyridine, or 1,8-diazabicyclo[5.4.0]undec-7-en (DBU).

For acylations, where Z is $COR^8$ or $CO_2$—$(C_1-C_6)$-alkyl, (VIII) is preferably an acid halide where $L^4$ is preferably chlorine or bromine (more preferably chlorine). A base is optionally present in the reaction, which is generally performed using similar bases, solvents and temperatures as employed for the alkylations.

For sulfonylations, where Z is $S(O)_pR^8$, (VIII) is preferably a sulfonyl halide where $L^4$ is preferably chlorine or bromine (more preferably chlorine). A base is optionally present in the reaction, which is generally performed using similar bases, solvents and temperatures as employed for the alkylations.

Collections of compounds of the formula (I) which can be synthesized by the above mentioned process may also be prepared in a parallel manner, and this may be effected manually or in a semiautomated or fully automated manner. In this case, it is possible, for example, to automate the procedure of the reaction, work-up or purification of the products or of the intermediates. In total, this is to be understood as meaning a procedure as is described, for example, by S. H. DeWitt in "Annual Reports in Combinatorial Chemistry and Molecular Diversity Automated Synthesis", Volume 1, Verlag Escom 1997, pages 69 to 77.

A series of commercially available apparatuses as are offered by, for example, Stem Corporation, Woodrolfe Road, Tollesbury, Essex, CM9 8SE, England or H+ P Labortechnik GmbH, Bruckmannring 28, 85764 Oberschleißheim, Germany or Radleys, Shirehill, Saffron Walden, Essex, England, may be used for the parallel procedure of the reaction and work-up. For the parallel purification of compounds of the formula (I), or of intermediates obtained during the preparation, use may be made, inter alia, of chromatography apparatuses, for example those by ISCO, Inc., 4700 Superior Street, Lincoln, Nebr. 68504, USA.

The apparatuses mentioned lead to a modular procedure in which the individual process steps are automated, but manual operations must be performed between the process steps. This can be prevented by employing semi-integrated or fully integrated automation systems where the automation modules in question are operated by, for example, robots. Such automation systems can be obtained, for example, from Zymark Corporation, Zymark Center, Hopkinton, Mass. 01748, USA.

In addition to what has been described here, compounds of the formula (I) may be prepared in part or fully by solid-phase-supported methods. For this purpose, individual intermediate steps or all intermediate steps of the synthesis or of a synthesis adapted to suit the procedure in question are bound to a synthetic resin. Solid-phase-supported synthesis methods are described extensively in the specialist literature, for example Barry A. Bunin in "The Combinatorial Index", Academic Press, 1998.

The use of solid-phase-supported synthesis methods permits a series of protocols which are known from the literature and which, in turn, can be performed manually or in an automated manner. For example, the "tea-bag method" (Houghten, U.S. Pat. No. 4,631,211; Houghten et al., Proc. Natl. Acad. Sci, 1985, 82, 5131-5135), in which products by IRORI, 11149 North Torrey Pines Road, La Jolla, Calif. 92037, USA, are employed, may be semiautomated. The automation of solid-phase-supported parallel syntheses is performed successfully, for example, by apparatuses by Argonaut Technologies, Inc., 887 Industrial Road, San Carlos, Calif. 94070, USA or MultiSynTech GmbH, Wullener Feld 4, 58454 Witten, Germany.

The preparation of the processes described herein yields compounds of the formula (I) in the form of substance collections which are termed libraries. The present invention also relates to libraries which comprise at least two compounds of the formula (I).

According to a further feature of the present invention there is provided a method for the control of pests at a locus which comprises applying thereto an effective amount of a compound of formula (I) or a salt thereof. For this purpose, the said compound is normally used in the form of a pesticidal composition (i.e. in association with compatible diluents or carriers and/or surface active agents suitable for use in pesticidal compositions), for example as hereinafter described.

The term "compound of the invention" as used hereinafter embraces a 5-substituted-alkylaminopyrazole of formula (I) as defined above and a pesticidally acceptable salt thereof.

One aspect of the present invention as defined above is a method for the control of pests at a locus. The locus includes, for example, the pest itself, the place (plant, field, forest, orchard, waterway, soil, plant product, or the like) where the pest resides or feeds, or a place susceptible to future infestation by the pest. The compound of the invention may therefore be applied directly to the pest, to the place where the pest resides or feeds, or to the place susceptible to future infestation by the pest.

As is evident from the foregoing pesticidal uses, the present invention provides pesticidally active compounds and methods of use of said compounds for the control of a number of pest species which includes: arthropods, especially insects or mites, or plant nematodes. The compound of the invention may thus be advantageously employed in practical uses, for example, in agricultural or horticultural crops, in forestry, in veterinary medicine or livestock husbandry, or in public health. The compounds of the invention may be used for example in the following applications and on the following pests:

For the control of soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

In the protection of stored products, for example cereals, including grain or flour, groundnuts, animal feedstuffs, timber or household goods, e.g. carpets and textiles, compounds of the invention are useful against attack by arthropods, more especially beetles, including weevils, moths or mites, for example *Ephestia* spp. (flour moths), *Anthrenus* spp. (carpet beetles), *Tribolium* spp. (flour beetles), *Sitophilus* spp. (grain weevils) or *Acarus* spp. (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack an building by termites, for example, *Reticulitermes* spp., *Heterotermes* spp., *Coptotermes* spp.

Moreover, it has been found that the compounds of the invention exhibit high insecticidal action against insects that destroy technical materials.

As example and preferably—but not limiting—the following insects are named:

Beetles such as *Hylotrupes bajulus, Chlorophorus pilosis, Anobium punctatum, Xestobium rufovillosum, Ptilinus pectiicornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;*

Hymenoptera such as *Sirex juvencus, Urocerus gigas, Urocerus gigas taignus, Urocerus augur;*

Termites such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Silverfish such as *Lepisma saccharina.*

Within the present context technical materials are understood to mean non-living materials such as preferably plastics, adhesives, glues, paper and cardboard, leather, wood, wood fabrication products and paints.

At the same time the compounds of the invention can be used for protection against fouling of objects, especially ships' hulls, screens, nets, buildings, wharfs and signal installations that come into contact with sea or brackish water.

Moreover, the compounds of the invention can be used in combination with other active compounds as anti-fouling agents.

The active compounds are suitable for the control of zoopests in household, hygiene and storage protection, especially insects, arachnids and mites that appear in enclosed spaces such as apartments, factory halls, offices, vehicle cabins, etc. They can be used alone or in combination with other active compounds and auxiliaries in household insecticidal products for the control of these pests. They are active against sensitive and resistant species as well as against all development stages. These pests include:

The order Scorpionidea e.g. *Buthus occitanus.*

The order Acarina e.g. *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae.*

The order Araneae e.g. *Aviculariidae, Araneidae.*

The order Opiliones e.g. *Pseudoscorpiones chelifer, Pseudoscorpiones cheiridium, Opiliones phalangium.*

The order Isopoda e.g. *Oniscus asellus, Porcellio scaber.*

The order Diplopoda e.g. *Blaniulus gultulatus, Polydesmus* spp.

The order Chilopoda e.g. *Geophilus* spp.

The order Zygentoma e.g. *Ctenolepisma* spp., *Lepisma saccharina, Lepismodes inquilinus.*

The order Blattaria e.g. *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa.*

The order Saltatoria e.g. *Acheta domesticus.*

The order Dermaptera e.g. *Forficula auricularia.*

The order Isoptera e.g. *Kalotermes* spp., *Reticulitermes* spp.

The order Psocoptera e.g. *Lepinatus* spp., *Liposcelis* spp.

The order Coleoptera e.g. *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum.*

The order Diptera e.g. *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa.*

The order Lepidoptera e.g. *Achroia grisella, Galleria mellonella, Plodia initerpunctella, Tinea cloacella, Tinea pellionella, Tineola bisselliella.*

The order Siphonaptera e.g. *Ctenocephalides canis, Ctenocephalides felis, Pulex irritans, Tunga penetrans, Xenopsylla cheopis.*

The order Hymenoptera e.g. *Camponotus herculeanus, Lasius fuliginosus, Lasius niger, Lasius umbratus, Monomorium pharaonis, Paravespula* spp., *Tetramorium caespitum.*

The order Anoplura e.g. *Pediculus humanus capitis, Pediculus humanus corporis, Pemphigus* spp., *Phylloera vastatrix, Phthirus pubis.*

The order Heteroptera e.g. *Cimex hemipterus, Cimex lectularius, Rhodinus prolixus, Triatoma infestans.*

The use in the household insecticidal sector is carried out alone or in combination with other suitable active compounds such as phosphates, carbamates, pyrethroids, neonicotinoids, growth regulators or active compounds from other known classes of insecticides.

Use is carried out with aerosols, non-pressurised spray agents, e.g. pump and dusting sprays, nebulisers, misters, foamers, gels, evaporation products with evaporation platelets of cellulose or plastic, liquid evaporators, gel and membrane evaporators, propeller-driven evaporators, non-energy or passive evaporation systems, fly papers, fly traps, and fly gels, as granulates or dusts, in scatter bait or bait stations.

In agriculture against adults, larvae and eggs of Lepidoptera (butterflies and moths), e.g. *Heliothis* spp. such as *Heliothis virescens* (tobacco budworm), *Heliothis armigera* and *Heliothis zea*. Against adults and larvae of Coleoptera (beetles) e.g. *Anthonomus* spp. e.g. grandis (cotton boll weevil), *Leptinotarsa decemlineata* (Colorado potato beetle), *Diabrotica* spp. (corn rootworms). Against Heteroptera (Hemiptera and Homoptera) e.g. *Psylla* spp., *Bemisia* spp., *Trialeurodes* spp., *Aphis* spp., *Myzus* spp., *Megoura viciae, Phylloxera* spp., *Nephotettix* spp. (rice leaf hoppers), *Nilaparvata* spp. Against Diptera e.g. *Musca* spp. Against Thysanoptera such as *Thrips tabaci*. Against Orthoptera such as *Locusta* and *Schistocerca* spp., (locusts and crickets) e.g. *Gryllus* spp., and *Acheta* spp. for example, *Blatta orientalis, Periplaneta americana, Blatella germanica, Locusta migratoria migratorioides,* and *Schistocerca gregaria.*

Against Collembola e.g. *Periplaneta* spp. and *Blatella* spp. (roaches). Against arthropods of agricultural significance such as Acari (mites) e.g. *Tetranychus* spp., and *Panonychus* spp.

Against nematodes which attack plants or trees of importance to agriculture, forestry or horticulture either directly or by spreading bacterial, viral, mycoplasma or fungal diseases of the plants. For example root-knot nematodes such as *Meloidogyne* spp. (e.g. *M. incognita*).

In the field of veterinary medicine or livestock husbandry or in the maintenance of public health against arthropods which are parasitic internally or externally upon vertebrates, particularly warm-blooded vertebrates, for example domestic animals, e.g. cattle, sheep, goats, equines, swine, poultry, dogs or cats, for example Acarina, including ticks (e.g. soft-bodied ticks including *Argasidae* spp. e.g. *Argas* spp. and *Ornithodorus* spp. (e.g. *Ornithodorus moubata*); hard-bodied ticks including *Ixodidae* spp., e.g. *Boophilus* spp. e.g. *Boophilus microplus, Rhipicephalus* spp. e.g. *Rhipicephalus appendiculatus* and *Rhipicephalus sanguineus*; mites (e.g. *Damalinia* spp.); fleas (e.g. *Ctenocephalides* spp. e.g. *Ctenocephalides felis* (cat flea) and *Ctenocephalides canis* (dog flea)); lice e.g. *Menopon* spp.; Diptera (e.g. *Aedes* spp., *Anopheles* spp., *Musca* spp., *Hypoderma* spp.); Hemiptera; Dictyoptera (e.g. *Periplaneta* spp., *Blatella* spp.); Hymenoptera; for example against infections of the gastrointestinal tract caused by parasitic nematode worms, for example members of the family Trichostrongylidae.

In a preferred aspect of the invention the compounds of formula (I) are used for the control of parasites of animals. Preferably the animal to be treated is a domestic companion animal such as a dog or a cat.

The parasites to be controlled include for example:

The order Anoplurida e.g. *Haematopinus* spp., *Linognathus* spp., *Pediculus* spp., *Phtirus* spp., *Solenopotes* spp.

The order Mallophagida and the suborders Amblycerina and Ischnocerina e.g. *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.

The order Diptera and the suborders Nematocerina and Brachycerina e.g. *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohifahrtia* spp., *Sarcophaga* spp., *Oestrus* spp., *Hypoderma* spp., *Gasterophilus* spp., *Hippobosca* spp., *Lipoptena* spp., *Melophagus* spp.

The order Siphonapterida e.g. *Pulex* spp., *Ctenocephalides* spp., *Xenopsylla* spp., *Ceratophyllus* spp.

The order Heteropterida e.g. *Cimex* spp., *Triatoma* spp., *Rhodnius* spp., *Panstrongylus* spp.

The order Blattarida e.g. *Blatta orientalis, Periplaneta americana, Blattela germanica, Supella* spp.

The subclass Acari (Acarina) and the order Meta- and Mesostigmata e.g. *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp., *Varroa* spp.

The order Actinedida (Prostigmata) and Acaridida (Astigmata) e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

The compounds of the invention of structure (I) are also suitable for the control of arthropods that affect agricultural animals such as cattle, sheep, goats, horses, pigs, donkeys, camels, buffalo, rabbits, chickens, turkeys, ducks, geese, bees, other domestic animals such as dogs, cats, cage birds, aquarium fish as well as so-called experimental animals such as hamsters, guinea pigs, rats and mice. By control of these arthropods death rates and performance loss (in meat, milk, wool, hides, eggs, honey, etc.) will be reduced so that a more economic and simpler animal husbandry is possible by the use of the compounds of the invention.

The use of the active compounds in veterinary sector and animal husbandry is carried out by known means by enteric administration in the form of, for example, tablets, capsules, drinks, drenches, granulates, pastes, boli, the feed-through process, suppositories, by parenteral administration by, for example, injection (intramuscular, subcutaneous, intravenous, interperitoneal, among others), implants, by nasal application, by dermal administration in the form of, for example, dipping, spraying, pour-on and spot-on, washing, powdering and with the help of appliances containing the active compound such as collars, ear markers, tail markers, limb bands, halters, marking devices, etc.

During use in cattle, poultry, domestic animals, etc., the active compounds of structure (I) can be used as formulations (for example, powder, emulsions, flowable agents) that contain the active compounds in an amount of 1 to 80 wt. %, directly or after 100 to 10,000 times dilution or as a chemical bath.

In a further aspect of the invention the compounds of formula (I) or salts or compositions thereof are used for the preparation of a veterinary medicament.

A further feature of the invention thus relates to the use of a compound of formula (I) or a salt thereof, or of a composition thereof, for the control of pests.

The above named pests include for example:

the order Anoplura (Phthiraptera) e.g. *Damalinia* spp., *Haematopinus* spp., *Linognathus* spp., *Pediculus* spp., *Trichodectes* spp.

The class of Arachnida e.g. *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici.*

The class of Bivalva e.g. *Dreissena* spp.

The order Chilopoda e.g. *Geophilus* spp., *Scutigera* spp.

The order Coleoptera e.g. *Acanthoscelides obtectus, Adoretus* spp., *Agelastica alni, Agriotes* spp., *Amphimallon soistitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnosterna consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Sternechus* spp., *Symphyletes* spp., *Tenebrio molitor, Tribolium* spp., *Trogoderma* spp., *Tychius* spp., *Xylotrechus* spp., *Zabrus* spp.

The order Collembola e.g. *Onychiurus armatus.*

The order Dermaptera e.g. *Forficula auricularia.*

The order Diplopoda e.g. *Blaniulus guttulatus.*

The order Diptera e.g. *Aedes* spp., *Anopheles* spp., *Bibio hortulanus, Calliphora erythrocephala, Ceratitis capitata, Chrysomyia* spp., *Cochliomyia* spp., *Cordylobia anthropophaga, Culex* spp., *Cuterebra* spp., *Dacus oleae, Dermatobia hominis, Drosophila* spp., *Fannia* spp., *Gastrophilus* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit, Pegomyia hyoscyami, Phorbia* spp., *Stomoxys* spp., *Tabanus* spp., *Tannia* spp., *Tipula paludosa, Wohlfahrtia* spp.

The class Gastropoda e.g. *Arion* spp., *Biomphalaria* spp., *Bulinus* spp., *Deroceras* spp., *Galba* spp., *Lymnaea* spp., *Oncomelania* spp., *Succinea* spp.

The class of Helminths e.g. *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp, *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria, Wuchereria bancrofti.*

In addition protozoa such as *Eimeria* may be controlled.

The order Heteroptera e.g. *Anasa tristis, Antestiopsis* spp., *Blissus* spp., *Calocoris* spp., *Campylomma livida, Cavelerius* spp., *Cimex* spp., *Creontiades dilutus, Dasynus piperis, Dichelops furcatus, Diconocoris hewetti, Dysdercus* spp., *Euschistus* spp., *Eurygaster* spp., *Heliopeltis* spp., *Horcias nobilellus, Leptocorisa* spp., *Leptoglossus phyllopus, Lygus* spp., *Macropes excavatus, Miridae, Nezara* spp., *Oebalus* spp., *Pentomidae, Piesma quadrata, Piezodorus* spp., *Psallus seriatus, Pseudacysta persea, Rhodnius* spp., *Sahlbergella singularis, Scotinophora* spp., *Stephanitis nashi, Tibraca* spp., *Triatoma* spp.

The order Homoptera e.g. *Acyrthosipon* spp., *Aeneolamia* spp., *Agonoscena* spp., *Aleurodes* spp., *Aleurolobus barodensis, Aleurothrixus* spp., *Amrasca* spp., *Anuraphis cardui, Aonidiella* spp., *Aphanostigma piri, Aphis* spp., *Arboridia apicalis, Aspidiella* spp., *Aspidiotus* spp., *Atanus* spp., *Aulacorthum solani, Bemisia* spp., *Brachycaudus helichrysii, Brachycolus* spp., *Brevicoryne brassicae, Calligypona marginata, Carneocephala fulgida, Ceratovacuna lanigera, Cercopidae, Ceroplastes* spp., *Chaetosiphon fragaefolii, Chionaspis tegalensis, Chlorita onukii, Chromaphis juglandicola, Chrysomphalus ficus, Cicadulina mbila, Coccomytilus halli, Coccus* spp., *Cryptomyzus ribis, Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus, Geococcus coffeae, Homalodisca coagulata, Hyalopterus arundinis, Icerya* spp., *Idiocerus* spp., *Idioscopus* spp., *Laodelphax striatellus, Lecanium* spp., *Lepidosaphes* spp., *Lipaphis erysimi, Macrosiphum* spp., *Mahanarva fimbriolata, Melanaphis sacchari, Metcalfiella* spp., *Metopolophium dirhodum, Monellia costalis, Monelliopsis pecanis, Myzus* spp., *Nasonovia ribisnigri, Nephotettix* spp., *Nilaparvata lugens, Oncometopia* spp., *Orthezia praelonga, Parabemisia myricae, Paratrioza* spp., *Parlatoria* spp., *Pemphigus* spp., *Peregrinus maidis, Phenacoccus* spp., *Phloeomyzus passerinii, Phorodon humuli, Phylloxera* spp., *Pinnaspis aspidistrae, Planococcus* spp., *Protopulvinaria pyriformis, Pseudaulacaspis pentagona, Pseudococcus* spp., *Psylla* spp., *Pteromalus* spp., *Pyrilla* spp., *Quadraspidiotus* spp., *Quesada gigas, Rastrococcus* spp., *Rhopalosiphum* spp., *Saissetia* spp.,

*Scaphoides titanus, Schizaphis graminum, Selenaspidus articulatus, Sogata* spp., *Sogatella furcifera, Sogatodes* spp., *Stictocephala festina, Tenalaphara malayensis, Tinocallis caryaefoliae, Tomaspis* spp., *Toxoptera* spp., *Trialeurodes vaporariorum, Trioza* spp., *Typhlocyba* spp., *Unaspis* spp., *Viteus vitifolii.*

The order Hymenoptera e.g. *Diprion* spp., *Hoplocampa* spp., *Lasius* spp., *Monomorium pharaonis, Vespa* spp.

The order Isopoda e.g. *Armadillidium vulgare, Oniscus asellus, Porcellio scaber.*

The order Isoptera e.g. *Reticulitermes* spp., *Odontotermes* spp.

The order Lepidoptera e.g. *Acronicta major, Aedia leucomelas, Agrotis* spp., *Alabama argillacea, Anticarsia* spp., *Barathra brassicae, Bucculatrix thurberiella, Bupalus piniarius, Cacoecia podana, Capua reticulana, Carpocapsa pomonella, Chematobia brumata, Chilo* spp., *Choristoneura fumiferana, Clysia ambiguella, Cnaphalocerus* spp., *Earias insulana, Ephestia kuehniella, Euproctis chrysorrhoea, Euxoa* spp., *Feltia* spp., *Galleria mellonella, Helicoverpa* spp., *Heliothis* spp., *Hofmannophila pseudospretella, Homona magnanima, Hyponomeuta padella, Laphygma* spp., *Lithocolletis blancardella, Lithophane antennata, Loxagrotis albicosta, Lymantria* spp., *Malacosoma neustria, Mamestra brassicae, Mocis repanda, Mythimna separata, Oria* spp., *Oulema oryzae, Panolis flammea, Pectinophora gossypiella, Phyllocnistis citrella, Pieris* spp., *Plutella xylostella, Prodenia* spp., *Pseudaletia* spp., *Pseudoplusia includens, Pyrausta nubilalis, Spodoptera* spp., *Thermesia gemmatalis, Tinea pellionella, Tineola bisselliella, Tortrix viridana, Trichoplusia* spp.

The order Orthoptera e.g. *Acheta domesticus, Blatta orientalis, Blattella germanica, Gryllotalpa* spp., *Leucophaea maderae, Locusta* spp., *Melanoplus* spp., *Periplaneta americana, Schistocerca gregaria.*

The order Siphonaptera e.g. *Ceratophyllus* spp., *Xenopsylla cheopis.*

The order Symphyla e.g. *Scutigerella immaculata.*

The order Thysanoptera e.g. *Baliothrips biformis, Enneothrips flavens, Frankliniella* spp., *Heliothrips* spp., *Hercinothrips femoralis, Kakothrips* spp., *Rhipiphorothrips cruentatus, Scirtothrips* spp., *Taeniothrips cardamoni, Thrips* spp.

The order Thysanura e.g. *Lepisma saccharina.*

The plant parasitic nematodes include, for example, *Anguina* spp., *Aphelenchoides* spp., *Belonoaimus* spp., *Bursaphelenchus* spp., *Ditylenchus dipsaci, Globodera* spp., *Heliocotylenchus* spp., *Heterodera* spp., *Longidorus* spp., *Meloidogyne* spp., *Pratylenchus* spp., *Radopholus similis, Rotylenchus* spp., *Trichodorus* spp., *Tylenchorhynchus* spp., *Tylenchulus* spp., *Tylenchulus semipenetrans, Xiphinema* spp.

The compounds of structure (I) of the invention are characterised particularly by strong action against aphids (e.g. *Aphis gossypii* and *Myzus persicae*), beetle larvae (e.g. *Phaedon cochleariae*), butterfly caterpillars (e.g. *Plutella xylostella, Spodoptera exigua* and *Spodoptera frugiperda*).

The compounds of the invention can optionally also be used in certain concentrations or application amounts as herbicides, safeners, growth regulators, or as agents for improving plant properties or as microbiocides, for example as fungicides, antimycotics, bactericides, viricides (including agents against viroids) or as agents against MLO (Mycoplasma-like organism) and RLO (Rickettsia-like organism). They may also be optionally used as intermediates or precursors for the synthesis of further active compounds.

According to the invention all plants and plant parts can be treated. Plants are hereby understood to mean all plants and plant populations such as desirable and undesirable wild plants or cultigens (including naturally occurring cultigens). Cultigens can be plants that can be obtained by conventional breeding and optimisation methods or by biotechnology or genetic engineering methods or combinations of these methods, including transgenic plants and including plant varieties that are protectable or not protectable by plant varieties protection rights. Plant parts are understood to be all above ground and below ground parts and organs of the plants such as scion, leaf, blossom and root, including, for example, leaves, needles, stalks, stems, blossoms, fruiting bodies, fruits and seed as well as roots, bulbs, rhizomes. Harvest crops as well as vegetative and generative reproduction material, for example cuttings, bulbs, rhizomes, shoots and seed also belong to plant parts.

In practical use for the control of arthropods, especially insects or mites, or helminths, especially nematode pests of plants, a method, for example, comprises applying to the plants or to the medium in which they grow an effective amount of a compound of the invention. For such a method, the compound of the invention is generally applied to the locus in which the arthropod or nematode infestation is to be controlled at an effective rate in the range of about 2 g to about 1 kg of the active compound per hectare of locus treated. Under ideal conditions, depending on the pest to be controlled, a lower rate may offer adequate protection. On the other hand, adverse weather conditions, resistance of the pest or other factors may require that the active ingredient be used at higher rates. The optimum rate depends usually upon a number of factors, for example, the type of pest being controlled, the type or the growth stage of the infested plant, the row spacing or also the method of application. Preferably an effective rate range of the active compound is from about 10 g/ha to about 400 g/ha, more preferably from about 50 g/ha to about 200 g/ha. When a pest is soil-borne, the active compound generally in a formulated composition, is distributed evenly over the area to be treated (for example broadcast or band treatment) in any convenient manner and is applied at rates from about 10 g/ha to about 400 g ai/ha, preferably from about 50 g/ha to about 200 g ai/ha. When applied as a root dip to seedlings or drip irrigation to plants the liquid solution or suspension contains from about 0.075 to about 1000 mg ai/l, preferably from about 25 to about 200 mg ai/l. Application may be made, if desired, to the field or crop-growing area generally or in close proximity to the seed or plant to be protected from attack. The compound of the invention can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting.

The compound of the invention and methods of control of pests therewith are of particular value in the protection of field, forage, plantation, glasshouse, orchard or vineyard crops, of ornamentals, or of plantation or forest trees, for example: cereals (such as wheat or rice), cotton, vegetables (such as peppers), field crops (such as sugar beets, soybeans or oil seed rape), grassland or forage crops (such as maize or sorghum), orchards or groves (such as of stone or pit fruit or citrus), ornamental plants, flowers or vegetables or shrubs under glass or in gardens or parks, or forest trees (both deciduous and evergreen) in forests, plantations or nurseries. They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compound of the invention and methods of use thereof are of particular value in the control of arthropods or helminths which are injurious to, or spread or act as vectors of diseases domestic animals, for example those hereinbefore mentioned, and more especially in the control of ticks, mites, lice, fleas, midges, or biting, nuisance or myiasis flies. The compounds of the invention are particularly useful in controlling arthropods or helminths which are present inside domestic host animals or which feed in or on the skin or suck the blood of the animal, for which purpose they may be administered orally, parenterally, percutaneously or topically.

The compositions hereinafter described for application to growing crops or crop growing loci or as a seed dressing may, in general, alternatively be employed in the protection of stored products, household goods, property or areas of the general environment. Suitable means of applying the compounds of the invention include: to growing crops as foliar sprays (for example as an in-furrow spray), dusts, granules, fogs or foams or also as suspensions of finely divided or encapsulated compositions as soil or root treatments by liquid drenches, dusts, granules, smokes or foams; to seeds of crops via application as seed dressings, e.g. by liquid slurries or dusts; to animals infested by or exposed to infestation by arthropods or helminths, by parenteral, oral or topical application of compositions in which the active ingredient exhibits an immediate and/or prolonged action over a period of time against the arthropods or helminths, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems; to the environment in general or to specific locations where pests may lurk, including stored products, timber, household goods, or domestic or industrial premises, as sprays, fogs, dusts, smokes, wax-smears, lacquers, granules or baits, or in tricklefeeds to waterways, wells, reservoirs or other running or standing water.

The compounds of formula (I) are particularly useful for the control of parasites of animals when applied orally, and in a further preferred aspect of the invention the compounds of formula (I) are used for the control of parasites of animals by oral application. The compounds of the formula (I) or salts thereof may be administered before, during or after meals. The compounds of the formula (I) or salts thereof may be mixed with a carrier and/or foodstuff.

The compound of the formula (I) or salt thereof is administered orally in a dose to the animal in a dose range generally from 0.1 to 500 mg/kg of the compound of the formula (I) or salt thereof per kilogram of animal body weight (mg/kg).

The frequency of treatment of the animal, preferably the domestic animal to be treated by the compound of the formula (I) or salt thereof is generally from about once per week to about once per year, preferably from about once every two weeks to once every three months.

The compounds of the invention may be administered most advantageously with another parasiticidally effective material, such as an endoparasiticide, and/or an ectoparasiticide, and/or an endectoparasiticide. For example, such compounds include macrocyclic lactones such as avermectins or milbemycins e.g., ivermectin, pyratel or an insect growth regulator such as lufenuron or methoprene.

The compounds of the formula (I) can also be employed for controlling harmful organisms in crops of known genetically engineered plants or genetically engineered plants yet to be developed. As a rule, the transgenic plants are distinguished by especially advantageous properties, for example by resistances to particular crop protection agents, resistances to plant diseases or pathogens of plant diseases, such as particular insects or microorganisms such as fungi, bacteria or viruses. Other particular properties concern, for example, the harvested material with regard to quantity, quality, storage properties, composition and specific constituents. Thus, transgenic plants are known where the starch content is increased, or the starch quality is altered, or where the harvested material has a different fatty acid composition.

All plants that have received by genetic engineering modification genetic material that imparts particularly advantageous valuable properties ("traits") to these plants belong to the transgenic (obtained by genetic engineering) plants or plant varieties to be preferably treated in accordance with the invention. Examples of such properties are improved plant growth, increased tolerance toward high or low temperatures, increased tolerance toward drought or toward water or soil salt content, improved blossoming performance, simplified harvesting, accelerated ripening, increased harvest yields, improved quality and/or nutritional value of the crop, better storage life and/or processing of the crop. Further and particularly emphasised examples of such properties are increased resistance of the plants toward zoopests and microbial pests, such as toward insects, mites, pathogenic plant fungi, bacteria and/or viruses as well as an increased tolerance of the plants toward certain herbicides. Examples of such transgenic plants are the important cultigens such as cereals (wheat, rice), maize, soy, potato, sugar beet, tomato, peas, and other vegetable varieties, cotton, tobacco, rape as well as fruit plants (with the fruits apple, pear, citrus fruits and grapes), whereby maize, soy, potato, cotton, tobacco and rape are especially emphasised. Properties ("traits") especially emphasised are the increased tolerance of the plants toward insects, arachnids, nematodes and gastropods through the toxins formed in the plants, especially those that are produced in the plants (hereinafter known as "Bt plants") by the genetic material from *Bacillus thuringiensis* (e.g. from the genes CryIA(a), CryIA(b), CryIA(c), CryIIA, CryIIIA, CryIIIB2, Cry9c Cry2Ab, Cry3Bb and CryIF as well as their combinations). Also particularly emphasised as properties ("traits") is the increased resistance of plants toward fungi, bacteria and viruses through systemically acquired resistance (SAR), systemin, phytoalexine, elicitors and resistance genes and correspondingly expressed proteins and toxins. Further particularly emphasised properties ("traits") are the increased tolerance of the plants to certain active herbicidal compounds, for example imidazolinones, sulphonylureas, glyphosate or phosphinotricin (e.g. "PAT"-gene). The respective genes imparting the desired properties ("traits") can also occur in the transgenic plants in combination with each other. Examples of such "Bt plants" are maize varieties, cotton varieties, soy varieties and potato varieties that are marketed under the trade marks YIELD GARD® (e.g. maize, cotton, soy), KnockOut® (e.g. maize), StarLink® (e.g. maize), Bollgard® (cotton), Nucotn® (cotton) and NewLeaf® (potato). Examples of herbicide tolerant plants are maize varieties, cotton varieties and soy varieties that are marketed under the trade marks Roundup Ready® (tolerance toward glyphosate, e.g. maize, cotton, soy), Liberty Link® (tolerance toward phosphinotricin, e.g. rape), IMI® (tolerance toward imidazolinones) and STS® (tolerance toward sulphonyl ureas, e.g. maize). Also mentioned as herbicide resistant (conventionally bred for herbicide tolerance) plants are those varieties marketed under the name Clearfield® (e.g. maize). Naturally these statements also apply to plant varieties developed or marketed in the future with these genetic properties ("traits") or those developed in the future.

The use in economically important transgenic crops of useful plants and ornamentals is preferred, for example of cereals such as wheat, barley, rye, oats, millet, rice, cassava and maize or else crops of sugar beet, cotton, soya, oilseed rape, potatoes, tomatoes, peas and other types of vegetables.

When used in transgenic crops, in particular those which have resistances to insects, effects are frequently observed, in addition to the effects against harmful organisms to be observed in other crops, which are specific for application in the transgenic crop in question, for example an altered or specifically widened spectrum of pests which can be controlled, or altered application rates which may be employed for application.

The Invention therefore also relates to the use of compounds of the formula (I) for controlling harmful organisms in transgenic crop plants.

According to a further feature of the present invention there is provided a pesticidal composition comprising one or more compounds of the invention as defined above, in association with, and preferably homogeneously dispersed in one or more compatible pesticidally acceptable diluents or carriers and/or surface active agents [i.e. diluents or carriers and/or surface active agents of the type generally accepted in the art as being suitable for use in pesticidal compositions and which are compatible with compounds of the Invention]. In practice, the compounds of the invention most frequently form parts of compositions. These compositions can be employed to control arthropods, especially insects, or plant nematodes or mites. The compositions may be of any type known in the art suitable for application to the desired pest in any premises or indoor or outdoor area. These compositions contain at least one compound of the invention as the active ingredient in combination or association with one or more other compatible components which are for example, solid or liquid carriers or diluents, adjuvants, surface-active-agents, or the like appropriate for the intended use and which are agronomically or medicinally acceptable. These compositions, which may be prepared by any manner known in the art, likewise form a part of this invention.

The compounds of the invention, in their commercially available formulations and in the use forms prepared from these formulations may be present in mixtures with other active substances such as insecticides, attractants, sterilants, acaricides, nematicides, fungicides, growth regulatory substances or herbicides.

The pesticides include, for example, phosphoric esters, carbamates, carboxylic esters, formamidines, tin compounds and materials produced by microorganisms.

Fungicides:

Nucleic Acid Synthesis Inhibitors
benalaxyl, benalaxyl-M, bupirimate, chiralaxyl, clozylacon, dimethirimol, ethirimol, furalaxyl, hymexazol, metalaxyl, metalaxyl-M, ofurace, oxadixyl, oxolinic acid Inhibitors of Mitosis and Cell Division
benomyl, carbendazim, diethofencarb, fuberidazole, pencycuron, thiabendazole, thiophanate-methyl, zoxamis Inhibitor of Respiratory Complex I
diflumetorim Inhibitors of Respiratory Complex II
boscalid, carboxin, fenfuram, flutolanil, furametpyr, mepronil, oxycarboxin, penthiopyrad, thifluzamide Inhibitor of Respiratory Complex III
azoxystrobin, cyazofamide, dimoxystrobin, enestrobin, famoxadone, fenamidone, fluoxastrobin, kresoximm-ethyl, metominostrobin, orysastrobin, pyraclostrobin, picoxystrobin Decouplers
dinocap, fluazinam Inhibitors of ATP Production
fentin acetate, fentin chloride, fentin hydroxide, silthiofam Inhibitor of Amino Acid and Protein Biosynthesis
andoprim, blasticidin-S, cyprodinil, kasugamycin, kasugamycin hydrochloride hydrate, mepanipyrim, pyrimethanil Inhibitors of Signal Transduction
fenpiclonil, fludioxonil, quinoxyfen Inhibitors of Fat and Membrane Synthesis
chlozolinate, iprodione, procymidone, vinclozolin
ampropylfos, potassium ampropylfos, edifenphos, iprobenfos (IBP), isoprothiolane, pyrazophos
tolciofos-methyl, biphenyl
iodocarb, propamocarb, propamocarb hydrochloride Inhibitors of Ergosterol Biosynthesis
fenhexamide,
azaconazole, bitertanol, bromuconazole, cyproconazole, diclobutrazole, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, paclobutrazole, penconazole, propiconazole, prothioconazole, simeconazole, tebuconazole, tetraconazole, triadimefon, triadimenol, triticonazole, uniconazole, voriconazole, imazalil, imazalil sulphate, oxpoconazole, fenarimol, flurprimidol, nuarimol, pyrifenox, triforin, pefurazoate, prochloraz, triflumizole, viniconazole,
aldimorph, dodemorph, dodemorph acetate, fenpropimorph, tridemorph, fenpropidin, spiroxamine,
naftifin, pyributicarb, terbinafin Inhibitors of Cell Wall Synthesis
benthiavalicarb, bialaphos, dimethomorph, flumorph, iprovalicarb, polyoxins, polyoxorim, validamycin A Inhibitors of Melanin Biosynthesis
capropamide, diclocymet, fenoxanil, phtalide, pyroquilon, tricyclazole Resistance Induction
acibenzolar-S-methyl, probenazole, tiadinil Multisite
captafol, captan, chlorothalonil, copper salts: copper hydroxide, copper naphthenate, copper oxychloride, copper sulphate, copper oxide, oxine-copper and Bordeaux mixture, dichlofluanid, dithianon, dodin, dodin freie base, ferbam, fluorofolpet, guazatin, guazatin acetate, iminoctadin, iminoctadine albesilate, iminoctadine triacetate, mancopper, mancozeb, maneb, metiram, metiram zinc, propineb, sulphur and sulphur preparations containing calcium polysulphide, thiram, tolylfluanid, zineb, ziram Unknown Mechanism amibromdol, benthiazole, bethoxazin, capsimycin, carvone, quinoline methionate, chloropicrin, cufraneb, cyflufenamide, cymoxanil, dazomet, debacarb, diclomezine, dichlorophen, dicloran, difenzoquat, difenzoquat methyl sulphate, diphenylamine, ethaboxam, ferimzone, flumetover, flusulfamide, fluopicolide, fluoroimide, hexachlorobenzene, 8-hydroxyquinoline sulphate, irumamycin, methasulphocarb, metrafenone, methyl isothiocyanate, mildiomycin, natamycin, nickel dimethyldithiocarbamate, nitrothal-isopropyl, octhilinone, oxamocarb, oxyfenthiin, pentachlorophenol and salts, 2-phenylphenol and salts, piperalin, propanosin-sodium, proquinazid, pyrrolnitrin, quintozen, tecloftalam, tecnazen, triazoxido, trichlamide, zarilamide and 2,3,5,6-tetrachloro-4-(methylsulphonyl)pyridine, N-(4-chloro-2-nitrophenyl)-N-ethyl-4-methylbenzenesulphonamide, 2-amino-4-methyl-N-phenyl-5-thiazole carboxamide, 2-chloro-N-(2,3-dihydro-1,1,3-trimethyl-1H-inden-4-yl)-3-pyridine carboxamide, 3-[5-(4-chlorophenyl)-2,3-dimethylisoxazolidin-3-yl]pyridine, cis-1-(4-chlorophenyl)-2-(1H-1,2,4-triazol-1-yl)cycloheptanol, 2,4-dihydro-5-methoxy-2-methyl-4-[[[[1-[3-(trifluoromethyl)-phenyl]ethyliden]amino]oxy]methyl]phenyl]-3H-1,2,3-triazol-3-one (185336-79-2), methyl 1-(2,3-dihydro-2,2-dimethyl-1H-inden-1-yl)-1H-imidazole-5-carboxylate, 3,4,5-trichloro-2,6-pyridine dicarbonitriel, methyl 2-[[[cyclopropyl[(4-methoxyphenyl) imino]methyl]thio]methyl]-.alpha.-(methoxymethylen)-benzacetate, 4-chloro-alpha-propinyloxy-N-[2-[3-methoxy-4-(2-propinyloxy)phenyl]ethyl]-benzacetamide, (2S)—N-[2-[4-[[3-(4-chlorophenyl)-2-propinyl]oxy]-3-methoxyphenyl]ethyl]-3-methyl-2-[(methylsulphonyl)amino]-butanamide, 5-chloro-7-(4-methylpiperidin-1-yl)-6-(2,4,6-trifluorophenyl)[1,2,4]triazolo[1,5-a]pyrimidine, 5-chloro-6-(2,4,6-trifluorophenyl)-N-[(1R)-1,2,2-trimethylpropyl][1,2,4]triazolo[1,5-a]pyrimidine-7-amine, 5-chloro-N-[(1R)-1,2-dimethylpropyl]-6-(2,4,6-trifluorophenyl)[1,2,4]triazolo[1,5-a]pyrimidine-7-amine, N-[1-(5-bromo-3-chloropyridin-2-yl)ethyl]-2,4-dichloronicotinamide, N-(5-bromo-3-chloropyridin-2-yl)methyl-2,4-dichloronicotinamide, 2-butoxy-6-iodo-3-propylbenzopyranon-4-one, N-(Z)-[(cyclopropylmethoxy)imino][6-(difluoromethoxy)-2,3-difluorophenyl]methyl)-2-benzacetamide, N-(3-ethyl-3,5,5-trimethylcyclohexyl)-3-formylamino-2-hydroxybenzamide, 2-[[[[1-[3-(1-fluoro-2-phenylethyl)oxy]phenyl ethylidene]amino]oxy]methyl]-alpha-(methoxyimino)-N-methyl-alphaE-benzacetamide, N-{2-[3-chloro-5-(trifluoromethyl)pyridin-2-yl]ethyl}-2-(trifluoromethyl)benzamide, N-(3',4'-dichloro-5-fluorobiphenyl-2-yl)-3-(difluoromethyl)-1-methyl-1H-pyrazole-4-carboxamide, N-(6-Methoxy-3-pyridinyl)-cyclopropane carboxamide, 1-[(4-methoxyphenoxy)methyl]-2,2-dimethylpropyl-1H-imidazole-1-carboxylic acid, O-[1-[(4-methoxyphenoxy)methyl]-2,2-dimethylpropyl]-1H-imidazole-1-carbothioic acid, 2-(2-{[6-(3-chlor-2-methylphenoxy)-5-fluoropyrimidin-4-yl]oxy}phenyl)-2-(methoxyimino)-N-methylacetamide Bactericides:

bronopol, dichlorophen, nitrapyrin, nickel dimethyldithiocarbamate, kasugamycin, octhilinon, furan carboxylic acid, oxytetracyclin, probenazol, streptomycin, tecloftalam, copper sulphate and other copper preparations.

Insecticide/Acaricide/Nematicide:

Acetylcholinesterase (AChE) inhibitors carbamates, for example alanycarb, aldicarb, aldoxycarb, allyxycarb, aminocarb, bendiocarb, benfuracarb, bufencarb, butacarb, butocarboxim, butoxycarboxim, carbaryl, carbofuran, carbosulfan, cloethocarb, dimetilan, ethiofencarb, fenobucarb, fenothiocarb, formetanate, furathiocarb, isoprocarb, metam-sodium, methiocarb, methomyl, metolcarb, oxamyl, pirimicarb, promecarb, propoxur, thiodicarb, thiofanox, trimethacarb, XMC, xylylcarb, triazamate organophosphates, for example acephate, azamethiphos, azinphos (-methyl, -ethyl), aromophos-ethyl, aromfenvinfos (-methyl), autathiofos, cadusafos, carbophenothion, chlorethoxyfos, chlorfenvinphos, chlormephos, chlorpyrifos (-methyl/-ethyl), coumaphos, cyanofenphos, cyanophos, chlorfenvinphos, demeton-5-methyl, demeton-5-methylsulphone, dialifos, diazinone, dichlofenthione, dichlorvos/DDVP, dicrotophos, dimethoate, dimethylvinphos, dioxabenzofos, disulfoton, EPN, ethion, ethoprophos, etrimfos, famphur, fenamiphos, fenitrothion, fensulfothion, fenthion, flupyrazofos, fonofos, formothion, fosmethilan, fosthiazate, heptenophos, iodofenphos, iprobenfos, isazofos, isofenphos, isopropyl O-salicylate, isoxathion, malathion, mecarbam, methacrifos, methamidophos, methidathion, mevinphos, monocrotophos, naled, omethoate, oxydemeton-methyl, parathion (-methyl/-ethyl), phenthoate, phorate, phosalone, phosmet, phosphamidone, phosphocarb, Phoxim, pirimiphos (-methyl/-ethyl), profenofos, propaphos, propetamphos, prothiofos, prothoate, pyraclofos, pyridaphenthion, pyridathion, quinalphos, sebufos, sulfotep, sulprofos, tebupirimfos, temephos, terbufos, tetrachlorvinphos, thiometon, triazophos, triclorfon, vamidothion Sodium channel modulators/voltage-dependent sodium channel blockers pyrethroids, for example acrinathrin, allethrin (d-cis-trans, d-trans), beta-cyfluthrin, bifenthrin, bioallethrin, bioallethrin-5-cyclopentyl-isomer, bioethanomethrin, biopermethrin, bioresmethrin, chlovaporthrin, cis-cypermethrin, cis-resmethrin, cis-permethrin, clocythrin, cyclopothrin, cyfluthrin, cyhalothrin, cypermethrin (alpha-, beta-, theta-, zeta), cyphenothrin, deltamethrin, empenthrin (1R-isomer), esfenvalerate, etofenprox, fenfluthrin, fenpropathrin, fenpyrithrin, fenvalerate, flubrocythrinate, flucythrinate, flufenprox, flumethrin, fluvalinate, fubfenprox, gamma-cyhalothrin, imiprothrin, kadethrin, lambda-cyhalothrin, metofluthrin, permethrin (cis-, trans-), phenothrin (1R-trans isomer), prallethrin, profluthrin, protrifenbute, pyresmethrin, resmethrin, RU 15525, silafluofen, tau-fluvalinate, tefluthrin, terallethrin, tetramethrin (-1R-isomer), tralomethrin, transfluthrin, ZXI 8901, pyrethrins (pyrethrum)

DDT oxadiazines, for example indoxacarb

Acetylcholine Receptor Agonists/Antagonists
  chloronicotinyls,
    for example acetamiprid, clothianidin, dinotefuran, imidacloprid, nitenpyram, nithiazine, thiacloprid, thiamethoxam
  nicotine, bensultap, cartap Acetylcholine Receptor Modulators
  Spinosynes,
    for example spinosad GABA Controlled Chloride Channel Antagonists
  Organochlorinee,
    for example camphechlor, chlordane, endosulfan, gamma-HCH, HCH, heptachlor, lindane, methoxychlor
  Fiproles,
    for example acetoprole, ethiprole, fipronil, pyrafluprole, pyriprole, vaniliprole Chloride Channel Activators
  Mectins,
    for example avermectin, emamectin, emamectin benzoate, ivermectin, milbemycin
  Juvenile hormone mimetics,
    for example diofenolan, epofenonane, fenoxycarb, hydroprene, kinoprene, methoprene, pyriproxifen, triprene Ecdysone Agonists/Disrupters
  diacylhydrazines,
    for example chromafenozide, halofenozide, methoxyfenozide, tebufenozide Inhibitors of Chitin Biosynthesis
  Benzoylureas,
    for example bistrifluoron, chlofluazuron, diflubenzuron, fluazuron, flucycloxuron, flufenoxuron, hexaflumuron, lufenuron, novaluron, noviflumuron, penfluoron, teflubenzuron, triflumuron
  buprofezin
  cyromazine Inhibitors of Oxidative Phosphorylation, ATP Disrupters
  diafenthiuron
  organotin compounds,
    for example azocyclotin, cyhexatin, fenbutatin-oxide Decouplers of Oxidative Phosphorylation by Interruption of H-Proton Gradients
  pyrrole,
    for example chlorfenapyr
  dinitrophenols,
    for example binapacyrl, dinobuton, dinocap, DNOC Site I Electron Transport Inhibitors
  METI's,
    for example fenazaquin, fenpyroximate, pyrimidifen, pyridaben, tebufenpyrad, tolfenpyrad
  hydramethylnon
  dicofol Site II Electron Transport Inhibitors
  rotenones Site III Electron Transport Inhibitors
  acequinocyl, fluacrypyrim Microbial Disrupters of Insect Intestinal Membrane
  *Bacillus thuringiensis* strains Inhibitors of Fat Synthesis
  tetronic acids,
    for example spirodiclofen, spiromesifen
  tetramic acids,
    for example spirotetramat (CAS-Reg.-No.: 203313-25-1) and 3-(2,5-dimethylphenyl)-8-methoxy-2-oxo-1-azaspiro[4.5]dec-3-en-4-yl ethyl carbonate (alias: carbonic acid, 3-(2,5-dimethylphenyl)-8-methoxy-2-oxo-1-azaspiro[4.5]dec-3-en-4-yl ethyl ester, CAS-Reg.-No.: 382608-10-8)
  carboxamides,
    for example flonicamid
  octopaminergic agonists,
    for example amitraz Inhibitor of Magnesium-Stimulated ATPase,
  propargite
  benzoic acid dicarboxamides,
    for example flubendiamide
  Nereistoxin analogous,
    for example thiocyclam hydrogen oxalate, thiosultap-sodium Agonists of the Ryanodin Receptor,
  benzoic acid dicarboxamides,
    for example flubendiamide Biologicals, Hormones or Pheromones
  azadirachtin, *Bacillus* spec., *Beauveria* spec., codlemone, *Metarrhizium* spec., *Paecilomyces* spec., thuringiensin, *Verticillium* spec.

Active Compounds with Unknown or Non-Specific Mode of Action
  fumigants,
    for example aluminium phosphide, methyl bromide, sulphuryl fluoride feeding inhibitors,
    for example cryolite, flonicamid, pymetrozine mite growth inhibitors,
    for example clofentezine, etoxazole, hexythiazox amidoflumet, benclothiaz, benzoximate, bifenazate, bromopropylate, buprofezin, quinomethionate, chlordimeform, chlorobenzilate, chloropicrin, clothiazoben, cycloprene, cyflumetofen, dicyclanil, fenoxacrim, fentrifanil, flubenzimine, flufenerim, flutenzin, gossyplure, hydramethylnone, japonilure, metoxadiazone, petroleum, piperonyl butoxide, potassium oleate, pyridalyl, sulfluramid, tetradifon, tetrasul, triarathene, verbutin A mixture with other known active compounds such as herbicides, fertilizers, growth regulators, safeners, semiochemicals or also with agents for improving plant properties is also possible.

The active compounds of the invention can also be present in their normal commercial formulations when used as insecticides as well as in the application forms prepared from these formulations in admixture with synergists. Synergists are compounds through which the activity of the active compound can be increased without the added synergist itself having to be active.

The active compounds of the invention can also be present in their normal commercial formulations when used as insecticides as well as in the application forms prepared from these formulations in admixture with inhibitors that reduce degradation of the active compound after use in the environment of the plants, on the surface of the plants or in plant tissues.

The abovementioned components for combinations are known active substances, many of which are described in Ch. R Worthing, S. B. Walker, The Pesticide Manual, 12 t" Edition, British Crop Protection Council, Farnham 2000.

The effective use doses of the compounds employed in the invention can vary within wide limits, particularly depending on the nature of the pest to be eliminated or degree of infestation, for example, of crops with these pests. In general, the compositions according to the invention usually contain about 0.05 to about 95% (by weight) of one or more active ingredients according to the invention, about 1 to about 95% of one or more solid or liquid carriers and, optionally, about 0.1 to about 50% of one or more other compatible components, such as surface-active agents or the like. In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant). The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminium or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or colouring agents which, when solid, may also serve as a diluent.

Suitable as solid carriers are:

for example, ammonium salts and natural mineral powders such a kaolin, clays, talc, chalk, quartz attapulgite, montmorillonite or diatomaceous earth, and synthetic mineral powders such as highly dispersed silica, aluminium oxide and silicates, suitable as carriers for granulates are: for example crushed and fractionated natural minerals such as calcite, marble, pumice, sepiolite, dolomite as well as synthetic granulates of inorganic and organic flours as well as granulates from organic materials such as paper, sawdust, coconut shells, maize ears and tobacco stalks; suitable as emulsifiers and foaming agents are; for example non-ionogenic and anionic emulsifiers such as polyoxyethylene fatty acid esters, polyoxyethylene fatty alcohol ethers, for example alkylarylpolyglycol ethers, alkylsulphonates, alkylsulphates, arylsulphonates and protein hydrolysates; suitable as dispersant are non-ionic and/or ionic materials, for example from the class of alcohol-POE and/or POP ethers, acid- and/or POP or POE esters, alkyl-aryl- and/or POP or POE ethers, fat- and/or POP or POE adducts, POE- and/or POP-polyol derivates, POE- and/or POP-sorbitan or sugar adducts, alkyl or aryl sulphates, sulphonates and phosphates or the respective PO ether adducts. In addition suitable oligo- or polymers, for example starting from vinylic monomers, of acrylic acid, from EO and/or PO alone or in combination with, for example (poly)alcohols or (poly)amines. In addition lignin and its sulphonic acid derivatives, simple and modified celluloses, aromatic and/or aliphatic sulphonic acids as well as their adducts with formaldehyde can be used.

Deposit builders such as carboxymethylcellulose, natural and synthetic powdery, granular or latex-like polymers can be used in the formulations, such as gum arabic, polyvinyl alcohol, polyvinyl acetate as well as natural phospholipids such a cephalins and lecithins and synthetic phospholipids.

The carrier may also be liquid, for example: water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or alkyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulphoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Amongst these are e.g., salts of polyacrylic acids, salts of lignosulphonic acids, salts of phenolsulphonic or naphthalenesulphonic acids, polycondensates of ethylene oxide with fatty alcohols or fatty acids or fatty esters or fatty amines, substituted phenols (particularly alkylphenols or arylphenols), salts of sulphosuccinic acid esters, taurine derivatives (particularly alkyltaurates), phosphoric esters of alcohols or of polycondensates of ethylene oxide with phenols, esters of fatty acids with polyols, or sulphate, sulphonate or phosphate functional derivatives of the above compounds. The presence of at least one surface-active agent is generally essential when the active ingredient and/or the inert carrier are only slightly water soluble or are not water soluble and the carrier agent of the composition for application is water. Compositions of the invention may further contain other additives such as adhesives or colorants. Adhesives such as carboxymethylcellulose or natural or synthetic polymers in the form of powders, granules or lattices, such as arabic gum, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

For their agricultural application, the compounds of the invention are therefore generally in the form of compositions, which are in various solid or liquid forms. Solid forms of compositions which can be used are dusting powders (with a content of the compound of the invention, ranging up to 80%), wettable powders or granules (including water dispersible granules), particularly those obtained by extrusion, compacting, impregnation of a granular carrier, or granulation starting from a powder (the content of the compound of the invention, in these wettable powders or granules being between about 0.5 and about 80%). Solid homogenous or heterogenous compositions containing one or more compounds of the invention, for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the active ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the prevent invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (e.g. low or ultra-low volume) depending upon the need or application technique. The compound or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as anti-foaming agents, corrosion inhibitors, stabilizers, penetrating agents, adhesives and, as the carrier, water or an organic liquid in which the active ingredient is poorly soluble or insoluble Some organic solids or inorganic salts may be dissolved in the carrier to help prevent settling or as antifreezes for water.

The wettable powers (or powder for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient is thoroughly mixed in a suitable blender with additional substances which may be impregnated on the porous filler and is ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. 1 to 200% by weight, or with an aqueous solution of a dispersing agent or binder, followed by drying and screening), or by a dry route (compacting followed by grinding and screening).

The rates and concentrations of the formulated compositions may vary according to the method of application or the nature of the compositions or use thereof. Generally speaking, the compositions for application to control arthropod or plant nematode pests usually contain from about 0.00001% to about 95%, more particularly from about 0.0005% to about 50% by weight of one or more compounds of the invention, or of total active ingredients (that is to say the compounds of the invention, together with other substances toxic to arthropods or plant nematodes, synergists, trace elements or stabilizers). The actual compositions employed and their rate of application will be selected to achieve the desired effect(s) by the farmer, livestock producer, medical or veterinary practitioner, pest control operator or other person skilled in the art.

Solid or liquid compositions for application topically to animals, timber, stored products or household goods usually contain from about 0.00005% to about 90%, more particularly from about 0.001% to about 10%, by weight of one or more compounds of the invention. For administration to animals orally or parenterally, including percutaneously solid or liquid compositions, these normally contain from about 0.1% to about 90% by weight of one or more compounds of the invention.

Medicated feedstuffs normally contain from about 0.001% to about 3% by weight of one or more compounds of the invention. Concentrates or supplements for mixing with feedstuffs normally contain from about 5% to about 90%, preferably from about 5% to about 50%, by weight of one or more compounds of the invention. Mineral salt licks normally contain from about 0.1% to about 10% by weight of one or more compounds of formula (I) or pesticidally acceptable salts thereof.

Dusts or liquid compositions for application to livestock, goods, premises or outdoor areas may contain from about 0.0001% to about 15%, more especially from about 0.005% to about 2.0%, by weight, of one or more compounds of the invention.

Suitable concentrations in treated waters are between about 0.0001 ppm and about 20 ppm, more particularly about 0.001 ppm to about 5.0 ppm. of one or more compounds of the invention, and may be used therapeutically in fish farming with appropriate exposure times. Edible baits may contain from about 0.01% to about 5%, preferably from about 0.01% to about 1.0%, by weight, of one or more compounds of the invention.

When administered to vertebrates parenterally, orally or by percutaneous or other means, the dosage of compounds of the invention, will depend upon the species, age, or health of the vertebrate and upon the nature and degree of its actual or potential infestation by arthropod or helminth pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily doses required over a period of months may be combined and administered to animals on a single occasion.

The following composition A-M (comp. A-M) illustrate compositions for use against arthropods, especially mites or insects, or plant nematodes, which comprise, as active ingredient, compounds of the invention, e.g. such as those described in preparative examples. The compositions described in comp. A-M can each be diluted to give a sprayable composition at concentrations suitable for use in the field.

Generic chemical descriptions of the ingredients (for which all of the following percentages are in weight percent), used in the composition A-M exemplified below, are as follows:

| Trade Name | Chemical Description |
|---|---|
| Ethylan BCP | Nonylphenol ethylene oxide condensate |
| Soprophor BSU | Tristyrylphenol ethylene oxide condensate |
| Arylan CA | A 70% w/v solution of calcium dodecylbenzenesulfonate |
| Solvesso 150 | Light C10 aromatic solvent |
| Arylan S | Sodium dodecylbenzenesulfonate |
| Darvan N02 | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

Composition A

A water soluble concentrate is prepared with the composition as follows:

| | |
|---|---|
| Active ingredient | 7% |
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

Composition B

An emulsifiable concentrate (EC) is prepared with the composition as follows:

| | |
|---|---|
| Active ingredient | 25% (max) |
| Soprophor BSU | 10% |
| Arylan CA | 5% |
| N-methylpyrrolidone | 50% |
| Solvesso 150 | 10% |

The first three components are dissolved in N-methylpyrrolidone and to this is then added the Solvesso 150 to give the final volume.

Composition C

A wettable powder (WP) is prepared with the composition as follows:

| | |
|---|---|
| Active ingredient | 40% |
| Arylan S | 2% |
| Darvan N02 | 5% |
| Celite PF | 53% |

The ingredients are mixed and ground in a hammer-mill to a powder with a particle size of less than 50 microns.

Composition D

An aqueous-flowable formulation is prepared with the composition as follows:

| | |
|---|---|
| Active ingredient | 40.00% |
| Ethylan BCP | 1.00% |
| Sopropon T360. | 0.20% |
| Ethylene glycol | 5.00% |
| Rhodigel 230. | 0.15% |
| Water | 53.65% |

The ingredients are intimately mixed and are ground in a bead mill until a mean particle size of less than 3 microns is obtained.

Composition E

An emulsifiable suspension concentrate is prepared with the composition as follows:

| | |
|---|---|
| Active ingredient | 30.0% |
| Ethylan BCP | 10.0% |
| Bentone 38 | 0.5% |
| Solvesso 150 | 59.5% |

The ingredients are intimately mixed and ground in a bead-mill until a mean particle size of less than 3 microns is obtained.

Composition F

A water dispersible granule is prepared with the composition as follows:

| | |
|---|---|
| Active ingredient | 30% |
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

Composition G

A dusting powder is prepared with the composition as follows:

| | |
|---|---|
| Active ingredient | 1 to 10% |
| Talc powder-superfine | 99 to 90% |

The ingredients are intimately mixed and further ground as necessary to achieve a fine powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

Composition H
An edible bait is prepared with the composition as follows:

| Active ingredient | 0.1 to 1.0% |
|---|---|
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

Composition I
A solution formulation is prepared with a composition as follows:

| Active ingredient | 15% |
|---|---|
| Dimethyl sulfoxide | 85% |

The active ingredient is dissolved in dimethyl sulfoxide with mixing and or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

Composition J
A wettable powder is prepared with the composition as follows:

| Active ingredient | 50% |
|---|---|
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infection by arthropods, by spraying or dipping, or by oral administration in drinking water, to control the arthropods.

Composition K
A slow release bolus composition is formed from granules containing the following components in varying percentages (similar to those described for the previous compositions) depending upon need:
Active ingredient,
Density agent,
Slow-release agent,
Binder.
The intimately mixed ingredients are formed into granules which are compressed into a bolus with a specific gravity of 2 or more. This can be administered orally to ruminant domestic animals for retention within the reticulo-rumen to give a continual slow release of active compound over an extended period of time to control infestation of the ruminant domestic animals by arthropods.

Composition L
A slow release composition in the form of granules, pellets, brickettes or the like can be prepared with compositions as follows:

| Active ingredient | 0.5 to 25% |
|---|---|
| Polyvinyl chloride | 75 to 99.5% |
| Dioctyl phthalate (plasticizer) | |

The components are blended and then formed into suitable shapes by melt-extrusion or molding. These composition are useful, for example, for addition to standing water or for fabrication into collars or eartags for attachment to domestic animals to control pests by slow release.

Composition M
A water dispersible granule is prepared with the composition as follows:

| Active ingredient | 85% (max) |
|---|---|
| Polyvinylpyrrolidone | 5% |
| Attapulgite clay | 6% |
| Sodium lauryl sulfate | 2% |
| Glycerine | 2% |

The ingredients are mixed as a 45% slurry with water and wet milled to a particle size of 4 microns, then spray-dried to remove water.

CHEMICAL EXAMPLES

NMR spectra were run in deuterochloroform unless stated otherwise, and shifts are given in ppm.
In the Examples which follow, quantities (also percentages) are weight based, unless stated otherwise.

Example 1

1-[2,6-dichloro-4-(trifluoromethyl)phenyl]-5-[(2,3-dihydroxypropyl)(methyl)amino]-4-[(trifluoromethyl)sulfonyl]-1H-pyrazole-3-carbonitrile To a mixture of 1-(2,6-dichloro-4-trifluoromethylphenyl)-3-cyano-5-bromo-4-trifluoromethylsulfonylpyrazole (6.00 g, 11.6 mmol) in THF (20 mL) 3-methylamino-1,2-propandiol (2.68 g, 25.5 mmol) was added. The mixture was heated to reflux for 6 h. Extractive workup (heptane-ethyl acetate, water) and recrystallisation from heptane-ethylacetate gave the title product (Compound 01-03, 3.40 g) as a white solid; $^1$H-NMR: 2.88 and 2.98 (NCH$_2$), 3.05 (NMe), 3.35 and 3.60 (CH$_2$O), 3.92 (CHO), 7.84 (ArH) ppm; $^{19}$F-NMR: −64.2 (PhCF$_3$); −78.9 ppm (SO$_2$CF$_3$).

Example 2

3-[{3-cyano-1-[2,6-dichloro-4-(trifluoromethyl)phenyl]-4-[(trifluoromethyl)sulfonyl]-1H-pyrazol-5-yl}(methyl)amino]propane-1,2-diyl diacetate To a mixture of 1-[2,6-dichloro-4-(trifluoromethyl)phenyl]-5-[(2,3-dihydroxypropyl)(methyl)amino]-4-[(trifluoromethyl)sulfonyl]-1H-pyrazole-3-carbonitrile (0.20 g, 0.4 mmol) in THF (4 mL) acetanhydride (75 mg, 0.7 mmol) and DMAP (14 mg, 0.1 mmol) was added. The mixture was heated to reflux for 5 h. Extractive workup (heptane-ethyl acetate, water) gave the title product (Compound 02-06, 0.20 g) as an oil; $^1$H-NMR: 1.98 and 2.08 (COCH$_3$), 3.05 (NMe), 3.05 and 3.15 (NCH$_2$), 3.88 and 4.16 (CH$_2$O), 5.11 (CHO), 7.85 (ArH) ppm; $^{19}$F-NMR: −64.2 (PhCF$_3$); −79.5 ppm (SO$_2$CF$_3$).

Example 3

1-[2,6-dichloro-4-(trifluoromethyl)phenyl]-5-(methyl [(2-oxo-1,3-dioxolan-4-yl)methyl]amino]-4-[(trifluoromethyl) sulfonyl]-1H-pyrazole-3-carbonitrile To a mixture of 1-[2,6-dichloro-4-(trifluoromethyl)phenyl]-5-[(2,3-dihydroxypropyl)(methyl)amino]-4-[(trifluoromethyl)sulfonyl]-1H-pyrazole-3-carbonitrile (0.20 g, 0.4 mmol) and diisopropylethylamin (0.14 g, 1.1 mmol) in THF (10 mL) phosgene-toluene solution (0.22 g, 20% COCl2, 0.4 mmol) was added. The mixture was stirred at 20-30° C. for 20 h. Extractive workup (heptane-ethyl acetate, water) and chromatography gave the title product (Compound 05-18, 0.14 g) as an oil; $^1$H-NMR: 2.88 (NMe), 3.35 and 3.45 (NCH$_2$), 3.96 and 4.55 (CH$_2$O), 4.82 (CHO), 7.87 (ArH) ppm; $^{19}$F-NMR: −63.8 (PhCF$_3$); -78.8 ppm (SO$_2$CF$_3$).

The following table 1 and 3 encompass compounds of formula (I) prepared in accordance with or analogously to the above described example 1. Table 2 and 4 encompass compounds of formula (I) prepared in accordance with or analogously to the above described example 2 and table 5 and 6 encompass compounds of formula (I) prepared in accordance with or analogously to the above described example 3.

Tables

TABLE 1

Compounds of Formula (I) in which the substituents have the following meanings:
$R^1$ is CN; $R^2$ is Cl; $R^3$, $R^5$ are CF$_3$; $R^4$ = CH$_3$; $R^{13}$ = H
$R^6$, $R^7$ = H, Alkyl

| Cpd number | $R^6$ | $R^7$ | n | mp. ° C., NMR(ppm) |
|---|---|---|---|---|
| 01-01 | H | H | 0 | |
| 01-02 | H | H | 1 | |
| 01-03 | H | H | 2 | 19F: −64.2; −78.9 |
| 01-04 | Me | Me | 0 | |
| 01-05 | Me | Me | 1 | |
| 01-06 | Me | Me | 2 | |
| 01-07 | Et | Et | 0 | |
| 01-08 | Et | Et | 1 | |
| 01-09 | Et | Et | 2 | |
| 01-10 | nPr | nPr | 0 | |
| 01-11 | nPr | nPr | 1 | |
| 01-12 | nPr | nPr | 2 | |
| 01-13 | iPr | iPr | 0 | |
| 01-14 | iPr | iPr | 1 | |
| 01-15 | iPr | iPr | 2 | |
| 01-16 | nBu | nBu | 0 | |
| 01-17 | nBu | nBu | 1 | |
| 01-18 | nBu | nBu | 2 | |
| 01-19 | secBu | secBu | 0 | |
| 01-20 | secBu | secBu | 1 | |
| 01-21 | secBu | secBu | 2 | |
| 01-22 | isoBu | isoBu | 0 | |
| 01-23 | isoBu | isoBu | 1 | |
| 01-24 | isoBu | isoBu | 2 | |
| 01-25 | tBu | tBu | 0 | |
| 01-26 | tBu | tBu | 1 | |

TABLE 1-continued

Compounds of Formula (I) in which the substituents have the following meanings:
$R^1$ is CN; $R^2$ is Cl; $R^3$, $R^5$ are CF$_3$; $R^4$ = CH$_3$; $R^{13}$ = H
$R^6$, $R^7$ = H, Alkyl

| Cpd number | $R^6$ | $R^7$ | n | mp. ° C., NMR(ppm) |
|---|---|---|---|---|
| 01-27 | tBu | tBu | 2 | |
| 01-28 | nC$_5$H$_{11}$ | nC$_5$H$_{11}$ | 0 | |
| 01-29 | nC$_5$H$_{11}$ | nC$_5$H$_{11}$ | 1 | |
| 01-30 | nC$_5$H$_{11}$ | nC$_5$H$_{11}$ | 2 | |
| 01-31 | nC$_5$H$_{13}$ | nC$_5$H$_{13}$ | 0 | |
| 01-32 | nC$_5$H$_{13}$ | nC$_5$H$_{13}$ | 1 | |
| 01-33 | nC$_5$H$_{13}$ | nC$_5$H$_{13}$ | 2 | |
| 01-34 | H | Me | 0 | |
| 01-35 | H | Me | 1 | |
| 01-36 | H | Me | 2 | |
| 01-37 | H | Et | 0 | |
| 01-38 | H | Et | 1 | |
| 01-39 | H | Et | 2 | |
| 01-40 | H | Ph | 0 | |
| 01-41 | H | Ph | 1 | |
| 01-42 | H | Ph | 2 | |
| 01-43 | Ph | Ph | 0 | |
| 01-44 | Ph | Ph | 1 | |
| 01-45 | Ph | Ph | 2 | |

TABLE 2

Compounds of Formula (I) in which the substituents have the following meanings:
$R^1$ is CN; $R^2$ is Cl; $R^3$, $R^5$ are CF$_3$; $R^4$ = CH$_3$; $R^{13}$ = H
$R^6$, $R^7$ = Acyl

| Cpd number | $R^6$ | $R^7$ | n | mp. ° C., NMR(ppm) |
|---|---|---|---|---|
| 02-01 | HCO | HCO | 0 | |
| 02-02 | HCO | HCO | 1 | |
| 02-03 | HCO | HCO | 2 | |
| 02-04 | CH$_3$CO | CH$_3$CO | 0 | |
| 02-05 | CH$_3$CO | CH$_3$CO | 1 | |
| 02-06 | CH$_3$CO | CH$_3$CO | 2 | 19F: −63.8; −78.5 |
| 02-07 | C$_2$H$_5$CO | C$_2$H$_5$CO | 0 | |
| 02-08 | C$_2$H$_5$CO | C$_2$H$_5$CO | 1 | |
| 02-09 | C$_2$H$_5$CO | C$_2$H$_5$CO | 2 | 19F: −63.8; −78.5 |
| 02-10 | nC$_3$H$_7$CO | nC$_3$H$_7$CO | 0 | |
| 02-11 | nC$_3$H$_7$CO | nC$_3$H$_7$CO | 1 | |
| 02-12 | nC$_3$H$_7$CO | nC$_3$H$_7$CO | 2 | |
| 02-13 | iC$_3$H$_7$CO | iC$_3$H$_7$CO | 0 | |
| 02-14 | iC$_3$H$_7$CO | iC$_3$H$_7$CO | 1 | |
| 02-15 | iC$_3$H$_7$CO | iC$_3$H$_7$CO | 2 | |
| 02-16 | nC$_4$H$_9$CO | nC$_4$H$_9$CO | 0 | |
| 02-17 | nC$_4$H$_9$CO | nC$_4$H$_9$CO | 1 | |
| 02-18 | nC$_4$H$_9$CO | nC$_4$H$_9$CO | 2 | |
| 02-19 | tBuCO | tBuCO | 0 | |
| 02-20 | tBuCO | tBuCO | 1 | |
| 02-21 | tBuCO | tBuCO | 2 | |
| 02-22 | PhCO | PhCO | 0 | |
| 02-23 | PhCO | PhCO | 1 | |
| 02-24 | PhCO | PhCO | 2 | |
| 02-25 | MeOCH$_2$CO | MeOCH$_2$CO | 0 | |
| 02-26 | MeOCH$_2$CO | MeOCH$_2$CO | 1 | |
| 02-27 | MeOCH$_2$CO | MeOCH$_2$CO | 2 | |
| 02-28 | EtOCH$_2$CO | EtOCH$_2$CO | 0 | |
| 02-29 | EtOCH$_2$CO | EtOCH$_2$CO | 1 | |
| 02-30 | EtOCH$_2$CO | EtOCH$_2$CO | 2 | |
| 02-31 | MeOCO | MeOCO | 0 | |
| 02-32 | MeOCO | MeOCO | 1 | |
| 02-33 | MeOCO | MeOCO | 2 | |
| 02-34 | EtOCO | EtOCO | 0 | |
| 02-35 | EtOCO | EtOCO | 1 | |
| 02-36 | EtOCO | EtOCO | 2 | |
| 02-37 | nPrOCO | nPrOCO | 0 | |
| 02-38 | nPrOCO | nPrOCO | 1 | |

TABLE 2-continued

Compounds of Formula (I) in which the substituents have the following meanings:
$R^1$ is CN; $R^2$ is Cl; $R^3$, $R^5$ are $CF_3$; $R^4 = CH_3$; $R^{13} = H$
$R^6$, $R^7$ = Acyl

| Cpd number | $R^6$ | $R^7$ | n | mp. °C., NMR(ppm) |
|---|---|---|---|---|
| 02-39 | nPrOCO | nPrOCO | 2 | |
| 02-40 | nBuOCO | nBuOCO | 0 | |
| 02-41 | nBuOCO | nBuOCO | 1 | |
| 02-42 | nBuOCO | nBuOCO | 2 | |
| 02-43 | CO—COOMe | CO—COOMe | 0 | |
| 02-44 | CO—COOMe | CO—COOMe | 1 | |
| 02-45 | CO—COOMe | CO—COOMe | 2 | |
| 02-46 | CO—COOEt | CO—COOEt | 0 | |
| 02-47 | CO—COOEt | CO—COOEt | 1 | |
| 02-48 | CO—COOEt | CO—COOEt | 2 | |

TABLE 3

Compounds of Formula (I) in which the substituents have the following meanings:
$R^1$ is CN; $R^2$ is Cl; $R^3$, $R^5$ are $CF_3$; $R^4 = H$; $R^{13} = H$
$R^6$, $R^7$ = H, Alkyl

| Cpd number | $R^6$ | $R^7$ | n | mp. °C., NMR(ppm) |
|---|---|---|---|---|
| 03-01 | H | H | 0 | |
| 03-02 | H | H | 1 | |
| 03-03 | H | H | 2 | |
| 03-04 | Me | Me | 0 | |
| 03-05 | Me | Me | 1 | |
| 03-06 | Me | Me | 2 | |
| 03-07 | Et | Et | 0 | |
| 03-08 | Et | Et | 1 | |
| 03-09 | Et | Et | 2 | |
| 03-10 | nPr | nPr | 0 | |
| 03-11 | nPr | nPr | 1 | |
| 03-12 | nPr | nPr | 2 | |
| 03-13 | iPr | iPr | 0 | |
| 03-14 | iPr | iPr | 1 | |
| 03-15 | iPr | iPr | 2 | |
| 03-16 | nBu | nBu | 0 | |
| 03-17 | nBu | nBu | 1 | |
| 03-18 | nBu | nBu | 2 | |
| 03-19 | secBu | secBu | 0 | |
| 03-20 | secBu | secBu | 1 | |
| 03-21 | secBu | secBu | 2 | |
| 03-22 | isoBu | isoBu | 0 | |
| 03-23 | isoBu | isoBu | 1 | |
| 03-24 | isoBu | isoBu | 2 | |
| 03-25 | tBu | tBu | 0 | |
| 03-26 | tBu | tBu | 1 | |
| 03-27 | tBu | tBu | 2 | |
| 03-28 | $nC_5H_{11}$ | $nC_5H_{11}$ | 0 | |
| 03-29 | $nC_5H_{11}$ | $nC_5H_{11}$ | 1 | |
| 03-30 | $nC_5H_{11}$ | $nC_5H_{11}$ | 2 | |
| 03-31 | $nC_6H_{13}$ | $nC_6H_{13}$ | 0 | |
| 03-32 | $nC_6H_{13}$ | $nC_6H_{13}$ | 1 | |
| 03-33 | $nC_6H_{13}$ | $nC_6H_{13}$ | 2 | |
| 03-34 | H | Me | 0 | |
| 03-35 | H | Me | 1 | |
| 03-36 | H | Me | 2 | |
| 03-37 | H | Et | 0 | |
| 03-38 | H | Et | 1 | |
| 03-39 | H | Et | 2 | |
| 03-40 | H | Ph | 0 | |
| 03-41 | H | Ph | 1 | |
| 03-42 | H | Ph | 2 | |
| 03-43 | Ph | Ph | 0 | |
| 03-44 | Ph | Ph | 1 | |
| 03-45 | Ph | Ph | 2 | |

TABLE 4

Compounds of Formula (I) in which the substituents have the following meanings:
$R^1$ is CN; $R^2$ is Cl; $R^3$, $R^5$ are $CF_3$; $R^4 = H$; $R^{13} = H$
$R^6$, $R^7$ = Acyl

| Cpd number | $R^6$ | $R^7$ | n | mp. °C., NMR(ppm) |
|---|---|---|---|---|
| 04-01 | HCO | HCO | 0 | |
| 04-02 | HCO | HCO | 1 | |
| 04-03 | HCO | HCO | 2 | |
| 04-04 | $CH_3CO$ | $CH_3CO$ | 0 | |
| 04-05 | $CH_3CO$ | $CH_3CO$ | 1 | |
| 04-06 | $CH_3CO$ | $CH_3CO$ | 2 | |
| 04-07 | $C_2H_5CO$ | $C_2H_5CO$ | 0 | |
| 04-08 | $C_2H_5CO$ | $C_2H_5CO$ | 1 | |
| 04-09 | $C_2H_5CO$ | $C_2H_5CO$ | 2 | |
| 04-10 | $nC_3H_7CO$ | $nC_3H_7CO$ | 0 | |
| 04-11 | $nC_3H_7CO$ | $nC_3H_7CO$ | 1 | |
| 04-12 | $nC_3H_7CO$ | $nC_3H_7CO$ | 2 | |
| 04-13 | $iC_3H_7CO$ | $iC_3H_7CO$ | 0 | |
| 04-14 | $iC_3H_7CO$ | $iC_3H_7CO$ | 1 | |
| 04-15 | $iC_3H_7CO$ | $iC_3H_7CO$ | 2 | |
| 04-16 | $nC_4H_9CO$ | $nC_4H_9CO$ | 0 | |
| 04-17 | $nC_4H_9CO$ | $nC_4H_9CO$ | 1 | |
| 04-18 | $nC_4H_9CO$ | $nC_4H_9CO$ | 2 | |
| 04-19 | tBuCO | tBuCO | 0 | |
| 04-20 | tBuCO | tBuCO | 1 | |
| 04-21 | tBuCO | tBuCO | 2 | |
| 04-22 | PhCO | PhCO | 0 | |
| 04-23 | PhCO | PhCO | 1 | |
| 04-24 | PhCO | PhCO | 2 | |
| 04-25 | $MeOCH_2CO$ | $MeOCH_2CO$ | 0 | |
| 04-26 | $MeOCH_2CO$ | $MeOCH_2CO$ | 1 | |
| 04-27 | $MeOCH_2CO$ | $MeOCH_2CO$ | 2 | |
| 04-28 | $EtOCH_2CO$ | $EtOCH_2CO$ | 0 | |
| 04-29 | $EtOCH_2CO$ | $EtOCH_2CO$ | 1 | |
| 04-30 | $EtOCH_2CO$ | $EtOCH_2CO$ | 2 | |
| 04-31 | MeOCO | MeOCO | 0 | |
| 04-32 | MeOCO | MeOCO | 1 | |
| 04-33 | MeOCO | MeOCO | 2 | |
| 04-34 | EtOCO | EtOCO | 0 | |
| 04-35 | EtOCO | EtOCO | 1 | |
| 04-36 | EtOCO | EtOCO | 2 | |
| 04-37 | nPrOCO | nPrOCO | 0 | |
| 04-38 | nPrOCO | nPrOCO | 1 | |
| 04-39 | nPrOCO | nPrOCO | 2 | |
| 04-40 | nBuOCO | nBuOCO | 0 | |
| 04-41 | nBuOCO | nBuOCO | 1 | |
| 04-42 | nBuOCO | nBuOCO | 2 | |
| 04-43 | CO—COOMe | CO—COOMe | 0 | |
| 04-44 | CO—COOMe | CO—COOMe | 1 | |
| 04-45 | CO—COOMe | CO—COOMe | 2 | |
| 04-46 | CO—COOEt | CO—COOEt | 0 | |
| 04-47 | CO—COOEt | CO—COOEt | 1 | |
| 04-48 | CO—COOEt | CO—COOEt | 2 | |

TABLE 5

Compounds of Formula (I) in which the substituents have the following meanings:
$R^1$ is CN; $R^2$ is Cl; $R^3$, $R^5$ are $CF_3$; $R^4 = CH_3$; $R^{13} = H$
$R^6$ and $R^7$ together with the OCH—$CH_2$O unit form a ring

| Cpd number | R6-R7 | n | mp. °C., NMR (ppm) |
|---|---|---|---|
| 05-01 | $CH_2$ | 0 | |
| 05-02 | $CH_2$ | 1 | |
| 05-03 | $CH_2$ | 2 | |
| 05-04 | $CMe_2$ | 0 | |
| 05-05 | $CMe_2$ | 1 | |
| 05-06 | $CMe_2$ | 2 | |
| 05-07 | CHPh | 0 | |
| 05-08 | CHPh | 1 | |
| 05-09 | CHPh | 2 | |

TABLE 5-continued

Compounds of Formula (I) in which the substituents have the following meanings:
$R^1$ is CN; $R^2$ is Cl; $R^3$, $R^5$ are $CF_3$; $R^4 = CH_3$; $R^{13} = H$
$R^6$ and $R^7$ together with the OCH—CH$_2$O unit form a ring

| Cpd number | R6-R7 | n | mp. °C., NMR (ppm) |
|---|---|---|---|
| 05- 10 | cyclopentan-1,1-diyl | 0 | |
| 05- 11 | cyclopentan-1,1-diyl | 1 | |
| 05- 12 | cyclopentan-1,1-diyl | 2 | |
| 05- 13 | cyclohexan-1,1-diyl | 0 | |
| 05- 14 | cyclohexan-1,1-diyl | 1 | |
| 05- 15 | cyclohexan-1,1-diyl | 2 | |
| 05- 16 | CO | 0 | |
| 05- 17 | CO | 1 | |
| 05- 18 | CO | 2 | 19F: −63.8; −78.8 |
| 05- 19 | CS | 0 | |
| 05- 20 | CS | 1 | |
| 05- 21 | CS | 2 | |
| 05- 22 | CO—CO | 0 | |
| 05- 23 | CO—CO | 1 | |
| 05- 24 | CO—CO | 2 | |
| 05- 25 | CH$_2$CO | 0 | |
| 05- 26 | CH$_2$CO | 1 | |
| 05- 27 | CH$_2$CO | 2 | |
| 05- 28 | 1,2-C$_6$H$_4$ | 0 | |
| 05- 29 | 1,2-C$_6$H$_4$ | 1 | |
| 05- 30 | 1,2-C$_6$H$_4$ | 2 | |
| 05- 31 | C$_2$H$_4$ | 0 | |
| 05- 32 | C$_2$H$_4$ | 1 | |
| 05- 33 | C$_2$H$_4$ | 2 | |
| 05- 34 | C$_3$H$_6$ | 0 | |
| 05- 35 | C$_3$H$_6$ | 1 | |
| 05- 36 | C$_3$H$_6$ | 2 | |
| 05- 37 | SO | 0 | |
| 05- 38 | SO | 1 | |
| 05- 39 | SO | 2 | |
| 05- 40 | SO$_2$ | 0 | |
| 05- 41 | SO$_2$ | 1 | |
| 05- 42 | SO$_2$ | 2 | |
| 05- 43 | PO(OH) | 0 | |
| 05- 44 | PO(OH) | 1 | |
| 05- 45 | PO(OH) | 2 | |
| 05- 46 | PO(OMe) | 0 | |
| 05- 47 | PO(OMe) | 1 | |
| 05- 48 | PO(OMe) | 2 | |
| 05- 49 | PO(OEt) | 0 | |
| 05- 50 | PO(OEt) | 1 | |
| 05- 51 | PO(OEt) | 2 | |
| 05- 52 | POPh | 0 | |
| 05- 53 | POPh | 1 | |
| 05- 54 | POPh | 2 | |
| 05- 55 | POMe | 0 | |
| 05- 56 | POMe | 1 | |
| 05- 57 | POMe | 2 | |

TABLE 6

Compounds of Formula (I) in which the substituents have the following meanings:
$R^1$ is CN; $R^2$ is Cl; $R^3$, $R^5$ are $CF_3$; $R^4 = H$; $R^{13} = H$
$R^6$ and $R^7$ together with the OCH—CH$_2$O unit form a ring

| Cpd number | R6-R7 | n | mp. °C., NMR (ppm) |
|---|---|---|---|
| 06- 01 | CH$_2$ | 0 | |
| 06- 02 | CH$_2$ | 1 | |
| 06- 03 | CH$_2$ | 2 | |
| 06- 04 | CMe$_2$ | 0 | |
| 06- 05 | CMe$_2$ | 1 | |
| 06- 06 | CMe$_2$ | 2 | |
| 06- 07 | CHPh | 0 | |
| 06- 08 | CHPh | 1 | |
| 06- 09 | CHPh | 2 | |
| 06- 10 | cyclopentan-1,1-diyl | 0 | |
| 06- 11 | cyclopentan-1,1-diyl | 1 | |
| 06- 12 | cyclopentan-1,1-diyl | 2 | |
| 06- 13 | cyclohexan-1,1-diyl | 0 | |
| 06- 14 | cyclohexan-1,1-diyl | 1 | |
| 06- 15 | cyclohexan-1,1-diyl | 2 | |
| 06- 16 | CO | 0 | |
| 06- 17 | CO | 1 | |
| 06- 18 | CO | 2 | |
| 06- 19 | CS | 0 | |
| 06- 20 | CS | 1 | |
| 06- 21 | CS | 2 | |
| 06- 22 | CO—CO | 0 | |
| 06- 23 | CO—CO | 1 | |
| 06- 24 | CO—CO | 2 | |
| 06- 25 | CH$_2$CO | 0 | |
| 06- 26 | CH$_2$CO | 1 | |
| 06- 27 | CH$_2$CO | 2 | |
| 06- 28 | 1,2-C$_6$H$_4$ | 0 | |
| 06- 29 | 1,2-C$_6$H$_4$ | 1 | |
| 06- 30 | 1,2-C$_6$H$_4$ | 2 | |
| 06- 31 | C$_2$H$_4$ | 0 | |
| 06- 32 | C$_2$H$_4$ | 1 | |
| 06- 33 | C$_2$H$_4$ | 2 | |
| 06- 34 | C$_3$H$_6$ | 0 | |
| 06- 35 | C$_3$H$_6$ | 1 | |
| 06- 36 | C$_3$H$_6$ | 2 | |
| 06- 37 | SO | 0 | |
| 06- 38 | SO | 1 | |
| 06- 39 | SO | 2 | |
| 06- 40 | SO$_2$ | 0 | |
| 06- 41 | SO$_2$ | 1 | |
| 06- 42 | SO$_2$ | 2 | |
| 06- 43 | PO(OH) | 0 | |
| 06- 44 | PO(OH) | 1 | |
| 06- 45 | PO(OH) | 2 | |
| 06- 46 | PO(OMe) | 0 | |
| 06- 47 | PO(OMe) | 1 | |
| 06- 48 | PO(OMe) | 2 | |
| 06- 49 | PO(OEt) | 0 | |
| 06- 50 | PO(OEt) | 1 | |
| 06- 51 | PO(OEt) | 2 | |
| 06- 52 | POPh | 0 | |
| 06- 53 | POPh | 1 | |
| 06- 54 | POPh | 2 | |
| 06- 55 | POMe | 0 | |
| 06- 56 | POMe | 1 | |
| 06- 57 | POMe | 2 | |

Biological Examples

Method A: Screening Method to Test Systemicity of Compounds Against *Ctenocephalides felis* (Cat Flea)

A test container was filled with 10 adults of *Ctenocephalides felis*. A glass cylinder was closed on one end with parafilm and placed on top of the test container. The test compound solution was then pipetted into bovine blood and added to the glass cylinder. The treated *Ctenocephalides felis* were held in this artificial dog test (blood 37° C., 40-60% relative humidity; *Ctenocephalides felis* 20-22° C., 40-60% relative humidity) and assessment performed at 24 and 48 hours after application. Compound 01-03, 02-09, 05-18, 05-45 gave at least 80% control of *Ctenocephalides felis* at a test concentration of 5 ppm or less.

Method B: Screening Method to Test Contact Activity Against *Rhipicephalus Sanguineus* (Brown Dog Tick)

Solutions of the test compounds were dropped onto filter paper, dried and the filter paper placed into test tubes and infested with 20-30 larvae (L1) of *Rhipicephalus sanguineus* and the tubes closed with a clip. The treated *Rhipicephalus sanguineus* were held in a climate chamber (25° C., 90% RH) and the percentage efficacy assessed 24 hours after application in comparison with the untreated control.

Compound numbers 05-45 gave at least 70% contact control of Rhipicephalus sanguineus at a test concentration of 100 ppm.

The invention claimed is:

1. A 5-aminoalkylaminopyrazole derivative of formula (I):

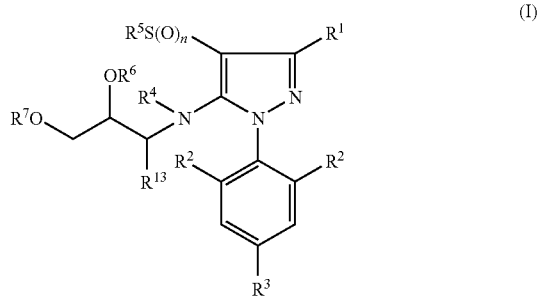

wherein
$R^1$ is CN, $CH_3$, $CF_3$, $C(=N-Z)-S(O)_p-(C_1-C_4)$-alkyl or $CSNH_2$; wherein Z is H, $(C_1-C_6)$-alkyl, $(C_1-C_6)$-haloalkyl, $(C_3-C_6)$-alkenyl, $(C_3-C_6)$-alkynyl, $-(CH_2)_qR^8$, $COR^9$, $CO_2-(C_1-C_6)$-alkyl or $S(O)_pR^9$;

$R^2$ for both residues independently from one another, is halogen, $CH_3$ or $NR^{11}R^{12}$;

$R^3$ is $(C_1-C_3)$-haloalkyl, $(C_1-C_3)$-haloalkoxy or $SF_5$;

$R^4$ is hydrogen, $(C_2-C_6)$-alkenyl, $(C_2-C_6)$-haloalkenyl, $(C_2-C_6)$-alkynyl, $(C_2-C_6)$-haloalkynyl, $(C_3-C_7)$-cycloalkyl, $(C_3-C_7)$-cycloalkyl-$(C_1-C_6)$-alkyl, $CO_2-(C_1-C_6)$-alkyl, $CO_2-(C_3-C_6)$-alkenyl, $CO_2-(C_3-C_6)$-alkynyl, $CO_2-(CH_2)_qR^8$, $CO_2-(CH_2)_qR^{10}$, $SO_2R^9$, Formyl, $CO-COO-(C_1-C_6)$-alkyl, $CO-(C_1-C_6)$-alkyl, $CO-(CH_2)_mR^8$, $CO-(CH_2)_mR^{10}$ or $(C_1-C_6)$-alkyl;

wherein the -alkenyl, -alkynyl, -cycloalkyl or -alkyl residues can be unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$-haloalkynyloxy, $(C_3-C_7)$-cycloalkyl, $S(O)_pR^9$, CN, $NO_2$, OH, $R^8$, $R^{10}$, $COR^9$, $NR^{11}R^{12}$, $OR^9$ and $CO_2R^9$;

$R^5$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl or $(C_2-C_6)$-haloalkynyl;

$R^6$ and $R^7$ are each independently H; or $(C_1-C_6)$-alkyl, $(C_1-C_6)$-haloalkyl, $(C_2-C_6)$-alkenyl, $(C_2-C_6)$-alkynyl, all of which can be substituted by one or more $R^8$, $R^{10}$, $R^9$ or $OR^9$ radicals;

or are each independently Acyl groups selected from the group consisting of formyl, $CO-(C_1-C_6)$-alkyl, $COO-(C_1-C_6)$-alkyl and $SO_2-(C_1-C_6)$-alkyl, wherein all of the alkyl residues may be unsubstituted or substituted by one or more radicals $R^9$; or $R^6$ and $R^7$ may together form a divalent group CO, CS, CO—CO, $CH_2CO$, $CHR^9CO$, $CR^9R^9CO$, SO, $SO_2$, PO(OH), $PO(OR^9)$, $PO(R^9)$, $PO(OR^{10})$, $PO(R^{10})$, $PO(OR^8)$, $PO(R^8)$, $(C_1-C_3)$-alkylene, $(C_3-C_7)$-cycloalkylene, $(C_3-C_7)$-cycloalkyl-$(C_1-C_6)$-alkylene, or 1,2-phenylene; all of which may be unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$-haloalkynyloxy, $(C_3-C_7)$-cycloalkyl, $S(O)_pR^9$, CN, $NO_2$, OH, $R^8$, $R^{10}$, $COR^9$, $NR^{11}R^{12}$, $OR^9$ and $CO_2R^9$; which together with the $C_2$ unit to which they are attached form a five to seven membered ring;

$R^8$ is phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^9$ and $NR^{11}R^{12}$;

$R^9$ is $(C_1-C_6)$-alkyl, $(C_1-C_6)$-haloalkyl, $(C_3-C_7)$-cycloalkyl, $-(C_1-C_4)$-alkyl-$(C_3-C_7)$-cycloalkyl, $-(CH_2)_qR^8$ or $-(CH_2)_qR^{10}$ $R^{10}$ is heterocyclyl unsubstituted or substituted by one or more radicals selected from the group consisting of halogen, $(C_1-C_4)$-alkyl, $(C_1-C_4)$-haloalkyl, $(C_1-C_4)$-alkoxy, $S(O)_pR^{13}$, OH and oxo;

$R^{11}$ and $R^{12}$ are each independently H; or $(C_1-C_6)$-alkyl, $(C_1-C_6)$-haloalkyl, $(C_2-C_6)$-alkenyl, $(C_2-C_6)$-alkynyl, all of which can be substituted by one or more $R^9$ or $OR^9$ radicals;

$R^{13}$ is hydrogen, $(C_1-C_6)$-alkyl or phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^9$ and $NR^{11}R^{12}$;

n and p and q are each independently zero, one or two;

m is zero, one, two or three; and each heterocyclyl in the above-mentioned radicals is independently a heterocyclic radical having 3 to 7 ring atoms and 1, 2 or 3 hetero atoms in the ring selected from the group consisting of N, O and S; or a pesticidally acceptable salt thereof.

2. A compound or a salt thereof as claimed in claim 1 wherein $R^6$ and $R^7$ is each independently from one another hydrogen, $(C_1-C_6)$-alkyl, $(C_1-C_6)$-haloalkyl, $(C_2-C_6)$-alkenyl, or $(C_2-C_6)$-alkynyl, wherein one or more hydrogen in the $(C_1-C_6)$-alkyl, $(C_1-C_6)$-haloalkyl, $(C_2-C_6)$-alkenyl, or $(C_2-C_6)$-alkenyl groups can be substituted by one or more radicals $R^9$ or $OR^9$; or $R^8$.

3. A compound or a salt thereof as claimed in claim 1 wherein $R^6$ and $R^7$ is each independently from one another formyl, $CO-(C_1-C_6)$-alkyl, $CO-(C_1-C_6)$-alkyl substituted by one or more radicals $R^9$, $COO-(C_1-C_6)$-alkyl, $COO-(C_1-C_6)$ alkyl substituted by one or more $R^9$ radicals, $CO-COO-(C_1-C_6)$-alkyl, $CO-COO-(C_1-C_6)$-alkyl substituted by one or more $R^9$ radicals, $SO_2-(C_1-C_6)$-alkyl, or $SO_2-(C_1-C_6)$-alkyl substituted by one or more $R^9$ radicals.

4. A compound or a salt thereof as claimed in claim 1 wherein $R^6$ and $R^7$ together form a divalent group CO, CS, CO—CO, $CH_2CO$, SO, $SO_2$, $PO(OH)_1$ $PO(OR^8)$, $PO(R^8)$, $PO(OR^9)$, or $PO(R^9)$, which together with the $C_2$ unit to which they are attached for a five to seven membered ring.

5. A compound or a salt thereof as claimed in claim 1 wherein $R^6$ and $R^7$ together form a divalent group $(C_1-C_3)$-alkylene, $(C_3-C_7)$-cycloalkylene, $(C_3-C_7)$-cycloalkyl-$(C_1-C_6)$-alkylene, or 1,2-phenylene, all of which are unsubstituted or substituted by one or more radicals selected from the group consisting of halogen, $(C_1-C_6$ alkoxy, $(C_1-C_6)$-haloalkoxy, $(C_3-C_6)$-alkenyloxy, $(C_3-C_6)$-haloalkenyloxy, $(C_3-C_6)$-alkynloxy, $(C_3-C_6)$-haloalkynyloxy, $(C_3-C_7)$-cycloalkyl, $S(O)_pR^9$, CN, $NO_2$, OH, $R^8$, $R^{10}$, $COR^9$, $NR^{11}R^{12}$, $OR^9$ or $CO_2R^9$; which together with the $C_2$ unit to which they are attached form a five to seven membered ring.

6. A compound or a salt thereof as claimed in claim 1 wherein
$R^1$ is CN, C(=N—Z)—$S(O)_p$—$(C_1-C_4)$-alkyl or $CSNH_2$; where Z is H, $(C_1-C_3)$-alkyl, —$(CH_2)_qR^8$, $COR^9$, $CO_2$—$(C_1-C_3)$-alkyl or $S(O)_pR^9$;
$R^2$ is halogen;
$R^3$ is $(C_1-C_3)$-haloalkyl;
$R^5$ is $(C_1-C_3)$-haloalkyl;
$R^{13}$ is hydrogen, $(C_1-C_3)$-alkyl, unsubstituted or substituted by one or more halogen;
$R^4$ is hydrogen, $(C_2-C_4)$-alkenyl, $(C_2-C_4)$-haloalkenyl, $(C_2-C_4)$-alkynyl, $(C_2-C_4)$-haloalkynyl, $(C_3-C_7)$-cycloalkyl, $(C_3-C_7)$-cycloalkyl-$(C_1-C_4)$-alkyl, $CO_2$-$(C_1-C_4)$-alkyl, $CO_2$—$(C_3-C_4)$-alkenyl, $CO_2$—$(C_3-C_4)$-alkynyl, $CO_2$—$(CH_2)_qR^8$, $CO_2$—$(CH_2)_qR^{10}$, $SO_2R^9$, formyl, CO—COO—$(C_1-C_4)$-alkyl, CO—$(C_1-C_4)$-alkyl or $(C_1-C_4)$-alkyl, unsubstituted or substituted by one or more radicals selected from the group consisting of halogen, $(C_1-C_3)$-alkyl, $(C_1-C_3)$-haloalkyl, $(C_1-C_3)$-alkoxy, $(C_1-C_3)$-haloalkoxy, $S(O)_pR^9$, CN and $NO_2$.

7. A process for the preparation of compounds of formula (I) or a salt thereof as defined in claim 1, wherein $R^1$ is CN, $CH_3$ or $CF_3$ which process comprises a) reacting a compound of formula (II)

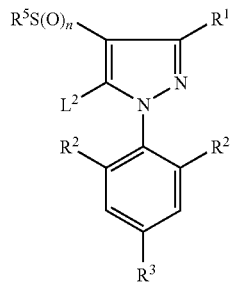

(II)

wherein
$L^2$ is a leaving group,
with a compound of formula (III):

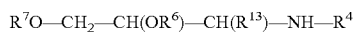

$R^7O$—$CH_2$—$CH(OR^6)$—$CH(R^{13})$—NH—$R^4$ (III)

or
b) reacting a compound of formula (IV)

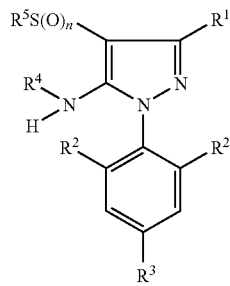

(IV)

with an alkylating agent of formula (III)

$R^7O$—$CH_2$—$CH(OR^6)$—$CH(R^{13})$-L (V)

wherein
L is a leaving group,
and a base, or
c) reacting a compound of formula (Ia),

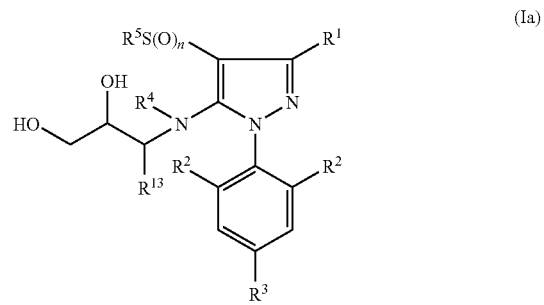

(Ia)

with an acylation agent $R^{14}$—COCl or $R^{14}$—CO—O—CO—$R^{15}$ or an acid dichloride selected from the group consisting of phosgene, oxalylchloride, thionylchloride, and phosphorus-dichlorides and a base, wherein $R^{14}$ and $R^{15}$ are independently H or $(C_1-C_6)$-alkyl, wherein the alkyl residue may be unsubstituted or substituted by one or more radicals $R^9$;
wherein
$R^2$ for both residues independently from one another, is selected from the group consisting of halogen, $CH_3$ or $NR^{11}R^{12}$;
$R^3$ is $(C_1-C_3)$-haloalkyl, $(C_1-C_3)$-haloalkoxy or $SF_5$;
$R^4$ is hydrogen, $(C_2-C_6)$-alkenyl, $(C_2-C_6)$-haloalkenyl, $(C_2-C_6)$-alkynyl, $(C_2-C_6)$-haloalkenyl, $(C_3-C_7)$-cycloalkyl, $(C_3-C_7)$-cycloalkyl-$(C_1-C_6)$-alkyl, $CO_2$—$(C_1-C_6)$-alkyl, $CO_2$—$(C_3-C_6)$-alkenyl, $CO_2$—$(C_3-C_6)$-alkynyl, $CO_2$—$(CH_2)_qR^8$, $CO_2$—$(CH_2)_qR^{10}$ or $SO_2R^9$; Formyl, CO—COO—$(C_1-C_6)$-alkyl or CO—$(C_1-C_6)$-alkyl or CO—$(CH_2)_mR^8$; CO—$(CH_2)_mR^{10}$ or $(C_1-C_6)$-alkyl
wherein the -alkenyl, -alkynyl, -cycloalkyl or -alkyl residues can be unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkenyloxy, $(C_3-C_6)$-haloalkynyloxy, $(C_3-C_7)$-cycloalkyl, $S(O)_pR^9$, CN, $NO_2$, OH, $R^8$, $R^{10}$, $COR^9$, $NR^{11}R^{12}$, $OR^9$ and $CO_2R^9$;
$R^5$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkenyl or $(C_2-C_6)$-haloalkynyl;
$R^6$ and $R^7$ are each independently H; or $(C_1-C_6)$-alkyl, $(C_1-C_6)$-haloalkyl, $(C_2-C_6)$-alkenyl, $(C_2-C_6)$-alkynyl, all of them can be substituted by one or more $R^8$, $R^{10}$, $R^9$ or $OR^9$ radicals; or are each independently Acyl groups selected from the group consisting of formyl, CO—$(C_1-C_6)$-alkyl COO—$(C_1-C_6)$-alkyl $SO_2$—$(C_1-C_6)$-alkyl, wherein all of the alkyl residues may be unsubstituted or substituted by one or more radicals $R^9$; or $R^6$ and $R^7$ may form a divalent group CO, CS, CO—CO, $CH_2CO$, $CHR^9CO$, $CR^9R^9CO$, SO, $SO_2$, PO(OH), $PO(OR^9)$, $PO(R^9)$, $PO(OR^{10})$, $PO(R^{10})$, $PO(OR^8)$, $PO(R^8)$, $(C_1-C_3)$-alkylene, $(C_3-C_7)$-cycloalkylene, $(C_3-C_7)(C_1-C_6)$-alkylene, or 1,2-phenylene; all of them unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$-haloalkynyloxy, $(C_3-C_7)$-cycloalkyl, $S(O)_pR^9$, CN, $NO_2$, OH, $R^8$, $COR^9$, $NR^{11}R^{12}$, $OR^9$ and $CO_2R^9$; which together with the $C_2$, unit to which they are attached form a five to seven membered ring;

$R^8$ is phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^9$ and $NR^{11}R^{12}$;

$R^9$ is $(C_1-C_6)$-alkyl, $(C_1-C_6)$-haloalkyl, $(C_3-C_7)$-cycloalkyl, $-(C_1-C_4)$-alkyl-$(C_3-C_7)$-cycloalkyl, $-CH_2)_qR^8$ or $—(CH_2)_qR^{10}$ $R^{10}$ is heterocyclyl unsubstituted or substituted by one or more radicals selected from the group consisting of halogen, $(C_1-C_4)$-alkyl, $(C_1-C_4)$-haloalkyl, $(C_1-C_4)$-alkoxy, $S(O)_pR^{13}$, OH and oxo;

$R^{11}$ and $R^{12}$ are each independently H; or $(C_1-C_6)$-alkyl, $(C_1-C_6)$-haloalkyl, $(C_2-C_6)$-alkenyl, $(C_2-C_6)$-alkynyl, all of them can be substituted by one or more $R^9$ or $OR^9$ radicals;

$R^{13}$ is hydrogen, $(C_1-C_6)$-alkyl or phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^9$ and $NR^{11}R^{12}$;

n and p and q are each independently zero, one or two;

m is zero, one, two or three; and d) optionally, converting a resulting compound of formula (I) into a pesticidally acceptable salt thereof.

8. A process for the preparation of compounds of formula (I) or a salt thereof as defined in claim 1,

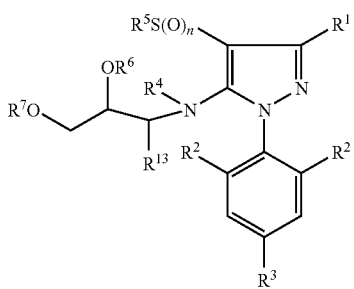

(I)

wherein $R^1$ is C(=N—Z)—S(O)_p—(C_1-C_4)-alkyl or $CSNH_2$ where Z is H, $(C_1-C_6)$-alkyl, $(C_1-C_6)$-haloalkyl, $(C_3-C_6)$-alkenyl, $(C_3-C_6)$-alkynyl, $—(CH_2)_qR^8$, $COR^9$, $CO_2$—$(C_1-C_6)$-alkyl or $S(O)_pR^9$;

$R^2$ for both residues independently from one another, is selected from the group consisting of halogen, $CH_3$ or $NR^{11}R^{12}$;

$R^3$ is $(C_1-C_3)$-haloalkyl, $(C_1-C_3)$-haloalkoxy $SF_5$;

$R^4$ is hydrogen, $(C_2-C_6)$-alkenyl, $(C_2-C_6)$-haloalkenyl, $(C_2-C_6)$-alkynyl, $(C_2-C_6)$-haloalkynyl, $(C_3-C_7)$-cycloalkyl, $(C_3-C_7)$-cycloalkyl-$(C_1-C_6)$-alkyl, $CO_2$—$(C_1-C_6)$-alkyl, $CO_2$—$(C_3-C_6)$-alkenyl, $CO_2$—$(C_3-C_6)$-alkynyl, $CO_2$—$(CH_2)_qR^8$, $CO_2$—$(CH_2)_qR^{10}$ or $SO_2R^9$; Formyl, CO—COO—$(C_1-C_6)$-alkyl or CO—$(C_1-C_6)$-alkyl or CO—$(CH_2)_mR^8$; CO—$(CH_2)_mR^{10}$ or $(C_1-C_6)$-alkyl wherein the -alkenyl, -alkynyl, -cycloalkyl or -alkyl residues can be unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$ haloalkynyloxy, $(C_3-C_7)$-cycloalkyl, $S(O)_pR^9$, CN, $NO_2$, OH, $R^8$, $R^{10}$, $COR^9$, $NR^{11}R^{12}$, $OR^9$ and $CO_2R^9$;

$R^5$ is $(C_1-C_6)$-alkyl, $(C_1-C_6)$-haloalkyl, $(C_2-C_6)$-alkenyl, $(C_2-C_6)$-haloalkenyl, $(C_2-C_6)$-alkynyl or $(C_2-C_6)$-haloalkynyl;

$R^6$ and $R^7$ are each independently H; or $(C_1-C_6)$-alkyl, $(C_1C_6)$-haloalkyl, $(C_2-C_6)$-alkenyl, $(C_2-C_6)$-alkynyl, all of them can be substituted by one or more $R^8$, $R^{10}$, $R^9$ or $OR^9$ radicals; or are each independently Acyl groups selected from the group consisting of formyl, CO—$(C_1-C_6)$-alkyl COO—$(C_1-C_6)$-alkyl $SO_2$—$(C_1-C_6)$-alkyl, wherein all of the alkyl residues may be unsubstituted or substituted by one or more radicals $R^9$; or $R^6$ and $R^7$ may form a divalent group CO, CS, CO—CO, $CH_2CO$, $CHR^9CO$, $CR^9R^9CO$, SO, $SO_2$, PO(OH), $PO(OR^9)$, $PO(R^9)$, $PO(OR^{10})$, $PO(R^{10})$, $PO(OR^8)$, $PO(R^8)$, $(C_1C_3)$-alkylene, $(C_3-C_7)$-cycloalkylene, $(C_3-C_7)$-cycloalkyl-$(C_1-C_6)$ alkylene, or 1,2-phenylene; all of them unsubstituted or substituted by one or more radicals selected from the group consisting of halogen, $(C_1-C_6)$-alkoxy, $(C_1-C_6)$-haloalkoxy, $(C_3-C_6)$-alkenyloxy, $(C_3-C_6)$-haloalkenyloxy, $(C_3-C_6)$-alkynyloxy, $(C_3-C_6)$-haloalkynyloxy, $(C_3-C_7)$-cycloalkyl, $S(O)_pR^2$, CN, $NO_2$, OH, $R_8$, $R_{10}$, $COR^9$, $NR^{11}R^{12}$, $OR^9$ and $CO_2R^9$; which together with the $C_2$, unit to which they are attached form a five to seven membered ring;

$R^8$ is phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^9$ and $NR^{11}R^{12}$;

$R^9$ is $(C_1-C_6)$-alkyl, $(C_1-C_6)$-haloalkyl$(C_3-C_7)$-cycloalkyl, —$(C_1-C_4)$-alkyl-$(C_3-C_7)$-cycloalkyl, —$(CH_2)_qR^8$ or —$(CH_2)_qR^{10}$ $R^{10}$ is heterocyclyl unsubstituted or substituted by one or more radicals selected from the group consisting of halogen, $(C_1-C_4)$-alkyl, $(C_1-C_4)$-haloalkyl, $(C_1-C_4)$-alkoxy, $S(O)_pR^{13}$, OH and oxo;

$R^{11}$ and $R^{12}$ are each independently H; or $(C_1-C_6)$-alkyl, $(C_1-C_6)$-haloalkyl, $(C_2-C_6)$-alkenyl, $(C_2-C_6)$-alkynyl, all of them can be substituted by one or more $R^9$ or $OR^9$ radicals;

$R^{13}$ is hydrogen, $(C_1-C_6)$-alkyl or phenyl unsubstituted or substituted by one or more radicals selected from the group consisting of halogen, $(C_1-C_6)$-alkyl, $(C_1-C_6)$-haloalkyl, $(C_1-C_6)$-alkoxy, $(C_1-C_6)$-haloalkoxy, CN, $NO_2$, $S(O)_pR^9$ and $NR^{11}R^{12}$; and n and p and q are each independently zero, one or two;

m is zero, one, two or three;

which process comprises a) where $R^1$ is $CSNH_2$ reacting the corresponding compound of formula (I) wherein $R^1$ is CN and and $R^2$, $R^3$, $R^4$, $R^5$, $R^6$, $R^7$, —$R^{13}$ and n are as defined above for formula (I), with an alkali or alkaline earth metal hydrosulfide or with the reagent $Ph_2PS_2$, or b) where $R^1$ is $CSNH_2$ reacting the corresponding compound of formula (I) wherein $R^1$ is CN, and $R^2$, $R^3$, $R^4$, $R^5$, $R^6$, $R^7$, —$R^{13}$ and n are as defined above for formula (I), and with a bis(trialkylsilyl)sulfide, in the presence of a base, or c) where $R^1$ is $C(=NH)—S—(C_1-C_4)$-alkyl reacting the corresponding compound of formula (I) wherein $R^1$ is $CSNH_2$, and $R^2, R^3, R^4, R^5, R^6, R^7, —R^{13}$ and n are as defined above for formula (I), with an alkylating agent of formula (VI) or (VII):

$(C_1-C_4)$-alkyl-$L^3$ (VI); $((C_1-C_4)$-alkyl$)_3O^+BF_4^-$ (VII)

where $L^3$ is a leaving group or d) where $R^1$ is $C(=NZ)—S—(C_1-C_4)$-alkyl and Z is $(C_1-C_6)$ alkyl, $(C_1-C_6)$-haloalkyl, $(C_3-C_6)$-alkenyl, $(C_3-C_6)$-alkynyl $—(CH_2)_qR^8$, $COR^9$, $CO_2—(C_1-C_6)$-alkyl or $S(O)_pR^9$; alkylating, acylating or sulfonylating the corresponding compound of formula (I) wherein $R^1$ is $C(=NZ)—S—(C_1-C_4)$-alkyl and Z is H, and $R^2, R^3, R^4, R^5, R^6, R^7, —R^{13}$ and n are as defined above for formula (I), with a compound of formula (VIII):

Z-$L^4$ (VIII)

wherein $L^4$ is a leaving group, and e) optionally, converting a resulting compound of formula (I) into a pesticidally acceptable salt thereof.

9. A pesticidal composition comprising a compound of formula (I) or a pesticidally acceptable salt thereof as defined in any one of claims 1 to 6, in association with a pesticidally acceptable diluent or carrier.

10. A method for the control of pests at a locus which comprises the application of an effective amount of a compound of formula (I) or a salt thereof as claimed in any of claims 1 to 6 or of a composition as claimed in claim 9 to the pests or the locus.

11. A method for the treatment of a parasitic infection or infestation in an animal, which comprises administering an effective amount of the compound of claim 1 to the animal in need thereof.

* * * * *